US011860273B2

(12) United States Patent
Kruse

(10) Patent No.: US 11,860,273 B2
(45) Date of Patent: Jan. 2, 2024

(54) SPATIAL AND TEMPORAL ENCODING OF TRANSMISSION FOR FULL SYNTHETIC TRANSMIT APERTURE IMAGING

(71) Applicant: Decision Sciences Medical Company, LLC, Poway, CA (US)

(72) Inventor: Dustin E. Kruse, Grand Island, NY (US)

(73) Assignee: DECISION SCIENCES MEDICAL COMPANY, LLC, Poway, CA (US)

(*) Notice: Subject to any disclaimer, the term of this patent is extended or adjusted under 35 U.S.C. 154(b) by 457 days.

(21) Appl. No.: 16/759,565

(22) PCT Filed: Oct. 27, 2018

(86) PCT No.: PCT/US2018/057891
§ 371 (c)(1),
(2) Date: Apr. 27, 2020

(87) PCT Pub. No.: WO2019/084526
PCT Pub. Date: May 2, 2019

(65) Prior Publication Data
US 2020/0284902 A1    Sep. 10, 2020

Related U.S. Application Data

(60) Provisional application No. 62/578,351, filed on Oct. 27, 2017.

(51) Int. Cl.
*G01S 15/89* (2006.01)
*A61B 8/00* (2006.01)
(Continued)

(52) U.S. Cl.
CPC ........ *G01S 15/8959* (2013.01); *A61B 8/4488* (2013.01); *A61B 8/5207* (2013.01);
(Continued)

(58) Field of Classification Search
None
See application file for complete search history.

(56) References Cited

U.S. PATENT DOCUMENTS

| 4,159,462 A | 6/1979 | Rocha et al. |
| 6,027,447 A * | 2/2000 | Li ..................... G01S 7/52049 |
| | | 600/447 |

(Continued)

FOREIGN PATENT DOCUMENTS

| JP | 55051351 A | 4/1980 |
| JP | 58195550 A | 11/1983 |

(Continued)

OTHER PUBLICATIONS

Extended European Search Report dated Jul. 7, 2021 in European Patent Application No. 18871063.6, 10 pages.

(Continued)

*Primary Examiner* — Isam A Alsomiri
*Assistant Examiner* — Joseph C Fritchman
(74) *Attorney, Agent, or Firm* — Perkins Coie LLP

(57) ABSTRACT

Techniques, systems, and devices are disclosed for spatial and temporal encoding of transmission in full synthetic transmit aperture imaging to achieve optimal spatial and contrast resolution and large signal-to-noise ratio for medical imaging applications with fewer signal transmissions, which can be equal to or less than the number of array elements within the aperture. In some aspects, a method of signal transmission is disclosed that includes a sequence of one or more sets of transmissions on a plurality of elements with unique, random, and/or optimized combinations of waveforms using amplitude and phase, and/or delay encoding. Sets of echoes corresponding to the sequence are beamformed such that fewer transmissions are needed than the number of array elements within the aperture, while maintaining complete spatial sampling of the aperture as if (Continued)

sampled according to a full set of synthetic transmit aperture transmissions on the same aperture.

27 Claims, 21 Drawing Sheets

(51) Int. Cl.
    *A61B 8/08*     (2006.01)
    *G10K 11/34*     (2006.01)

(52) U.S. Cl.
    CPC ............ *A61B 8/5269* (2013.01); *A61B 8/587* (2013.01); *G01S 15/8927* (2013.01); *G01S 15/8997* (2013.01); *G10K 11/346* (2013.01)

(56) References Cited

U.S. PATENT DOCUMENTS

| | | | |
|---|---|---|---|
| 6,736,780 B2 | 5/2004 | Song et al. | |
| 7,066,886 B2 | 6/2006 | Song et al. | |
| 8,002,705 B1* | 8/2011 | Napolitano | A61B 8/5246 |
| | | | 600/407 |
| 8,939,909 B2 | 1/2015 | Wegner | |
| 9,844,359 B2 | 12/2017 | Wegner | |
| 10,321,889 B2 | 6/2019 | Wegner | |
| 11,096,661 B2 | 8/2021 | Wegner | |
| 2002/0138002 A1* | 9/2002 | Tarakci | A61B 8/4472 |
| | | | 600/437 |
| 2003/0125628 A1 | 7/2003 | Song et al. | |
| 2005/0101867 A1 | 5/2005 | Johnson et al. | |
| 2007/0156050 A1 | 7/2007 | Barnes et al. | |
| 2007/0239002 A1 | 10/2007 | Alam | |
| 2008/0110263 A1 | 5/2008 | Klessel et al. | |
| 2010/0280381 A1* | 11/2010 | Madore | A61B 8/4483 |
| | | | 600/447 |
| 2012/0281507 A1 | 11/2012 | Rikoski | |
| 2014/0364737 A1 | 12/2014 | Huang et al. | |
| 2015/0080725 A1* | 3/2015 | Wegner | A61B 8/4461 |
| | | | 600/443 |
| 2015/0265250 A1 | 9/2015 | Madore | |
| 2016/0061950 A1 | 3/2016 | Xu et al. | |
| 2016/0065323 A1 | 3/2016 | Zemp | |
| 2016/0143617 A1* | 5/2016 | Ebbini | G01S 15/8915 |
| | | | 600/447 |
| 2016/0213258 A1* | 7/2016 | Lashkari | G01S 15/8915 |
| 2016/0249882 A1* | 9/2016 | Degertekin | A61B 8/56 |
| | | | 600/424 |
| 2016/0270763 A1* | 9/2016 | Hayes | G01S 15/8934 |
| 2017/0276775 A1 | 9/2017 | Tanter et al. | |

FOREIGN PATENT DOCUMENTS

| | | |
|---|---|---|
| JP | 60048736 A | 3/1985 |
| JP | 2004147852 A | 5/2004 |
| JP | 2013520235 | 6/2013 |

OTHER PUBLICATIONS

International Search Report and Written Opinion dated Jan. 17, 2019 for App. No. PCT/US18/57891; 11 pages.
Martin-Arguedas, C.J. et al., "An Ultrasonic Imaging System Based on a New SAFT Approach and a GPU Beamformer." IEEE Transactions on Ultrasonics, Ferroelectrics and Frequency Control. vol. 59, No. 7, Jul. 2012, 11 pages.
Romero-Laorden, D. et al., "Strategies for Hardware Reduction on the Design of Portable Ultrasound Imaging Systems." Chapter 9, INTECH, 2013, 26 pages.
European Search Report dated Apr. 19, 2017 for European Application No. 14844538.0, filed on Sep. 9, 2014 (10 pages).
Examination Report dated Dec. 20, 2019 for Europe Patent Application No. 14844538.0, filed on Sep. 9, 2014 (7 pages).
International Search Report and Written Opinion dated Mar. 3, 2015 for International Application No. PCT/US2014/054855, filed on Sep. 9, 2014 (11 pages).
Office Action dated Mar. 17, 2020 for Japanese Application No. 2018-145683, filed on Sep. 9, 2014 (4 pages).
Office Action dated Mar. 25, 2020 for Japanese Application No. 2016-542050, filed on Sep. 9, 2014 (4 pages).
Office Action dated Oct. 20, 2020 for Canadian Application No. 2,923,861, 4 pages.
Office Action dated Oct. 29, 2019 for Japanese Application No. 2018-145683, filed on Sep. 9, 2014 (3 pages).
Office Action dated Jun. 11, 2019 for Japanese Application No. 2016-542050, filed on Sep. 9, 2014 (15 pages).
Office Action dated Jun. 18, 2019 for Japanese Patent Application No. 2018-145683, filed on Sep. 9, 2014, 12 pages.
Office Action dated Jun. 5, 2018 for Chinese Patent Application No. 201480062224.3, filed on Sep. 9, 2014, 13 pages.
Office Action dated Sep. 19, 2017 for Japanese Application No. 2016-542050, filed on Sep. 9, 2014 (15 pages).
Singapore Written Opinion dated Jul. 10, 2017 for Singapore Application No. 11201601906P, filed on Sep. 9, 2014 (8 pages).

* cited by examiner

SPATIAL AND TEMPORAL ENCODING OF TRANSMISSION FOR FULL SYNTHETIC TRANSMIT APERTURE IMAGING

CROSS-REFERENCE TO RELATED APPLICATIONS

This patent document claims priorities to and benefits of U.S. Provisional Patent Application No. 62/578,351 entitled "SPATIAL AND TEMPORAL ENCODING OF TRANSMISSION FOR FULL SYNTHETIC TRANSMIT APERTURE IMAGING" and filed on Oct. 27, 2017. The entire content of the before-mentioned patent application is incorporated by reference as part of the disclosure of this document.

TECHNICAL FIELD

This patent document relates to systems, devices, and processes for imaging technologies that applicable to various medical imaging modalities.

BACKGROUND

Among various imaging modality, such as radar, lidar, optical, electromagnetic, microwave, terahertz, sonar, and photoacoustic imaging, acoustic imaging is a safe and relatively cheap imaging modality that employs the properties of sound waves traveling through a medium to render a visual image. High frequency acoustic imaging has been used as an imaging modality for decades in a variety of biomedical fields to view internal structures and functions of animals and humans. Fundamentally, ultrasound imaging operates the same principle as sound navigation and ranging (SONAR) in which a transmission of one or more acoustic waves results in one or more echoes from structures that are received and processed to form an image. Some factors, including inadequate spatial resolution and tissue differentiation, can lead to less than desirable image quality using conventional techniques of ultrasound imaging, which can limit its use for many clinical indications or applications.

SUMMARY

Techniques, systems, and devices are disclosed for spatial and temporal encoding of transmission in full synthetic transmit aperture imaging to achieve spatial and contrast resolution for medical imaging with fewer signal transmissions.

In some aspects, a method for spatial and temporal encoding of acoustic waveforms in synthetic aperture acoustic imaging includes generating a set of spatially and temporally encoded acoustic waveforms for transmission toward a target volume that includes generating one or more of (i) a unique set of coded waveforms, (ii) a transmit delay pattern of time delays for acoustic waveforms to be transmitted at the target volume, or (iii) a transmit amplitude and phase pattern of the acoustic waveforms to be transmitted at the target volume; coherently transmitting the spatially and temporally encoded acoustic waveforms, toward the target volume, using a spatially-sampled aperture formed on an array of transducer elements for one or more transducer segments of an acoustic probe device, wherein each transducer element used in the transmitting is assigned a first index number 1 to i, wherein i is a number equal to or less than a total number of transducer elements; receiving returned encoded acoustic waveforms on the spatially-sampled aperture, wherein the wherein the transducer elements are assigned a second index number 1 to j, wherein j is a number equal to or less than a total number of transducer elements; decoding the returned encoded acoustic waveforms to isolate the $i^{th}$ transmission on the $j^{th}$ reception that correspond to a set of image points of the target volume; and processing the decoded returned encoded acoustic waveforms to beamform isolated echo samples for each image point of the set of image points of the target volume.

In some aspects, a probe device to interface a body structure of a biological subject is disclosed. The device includes one or more transducer segments comprising an array of transducer elements, and a probe controller in communication with the array of transducer elements to select a first subset of transducer elements of the array to transmit waveforms, and to select a second subset of transducer elements of the array to receive returned waveforms, wherein the first subset of transducer elements are arranged to transmit the waveforms toward a target volume in the biological subject and the second subset of transducer elements are arranged to receive the returned waveforms that return from at least part of the target volume. The waveforms are transmitted in accordance with an encoding method that generates a predetermined (i) unique set of waveforms, (ii) transmit delay pattern, and/or (iii) transmit amplitude and phase pattern that spatially and temporally encodes the waveforms transmitted at the target volume; such that, after processing by a decoding method, waveform components corresponding to each transmit transducer element are separated from the waveforms on each receive transducer element resulting in a set of waveforms representative of a full synthetic transmit aperture acquisition.

In some aspects, a method for encoding acoustic signal transmissions is disclosed. The method comprises transmitting by a first transducer element, after a time delay associated with the first transducer element, waveforms towards a target volume in a biological subject; receiving by a second transducer element, after a round-trip time between the first transducer element and the second transducer element, returned waveforms that return from at least part of the target volume; identifying the first transducer element that contributes to the returned acoustic waveforms based on the time delay and the round trip-time; and processing the returned waveforms based on the identification of the first transducer element to generate an image of the target volume in the biological subject.

DETAILED DESCRIPTION

Figure 1:
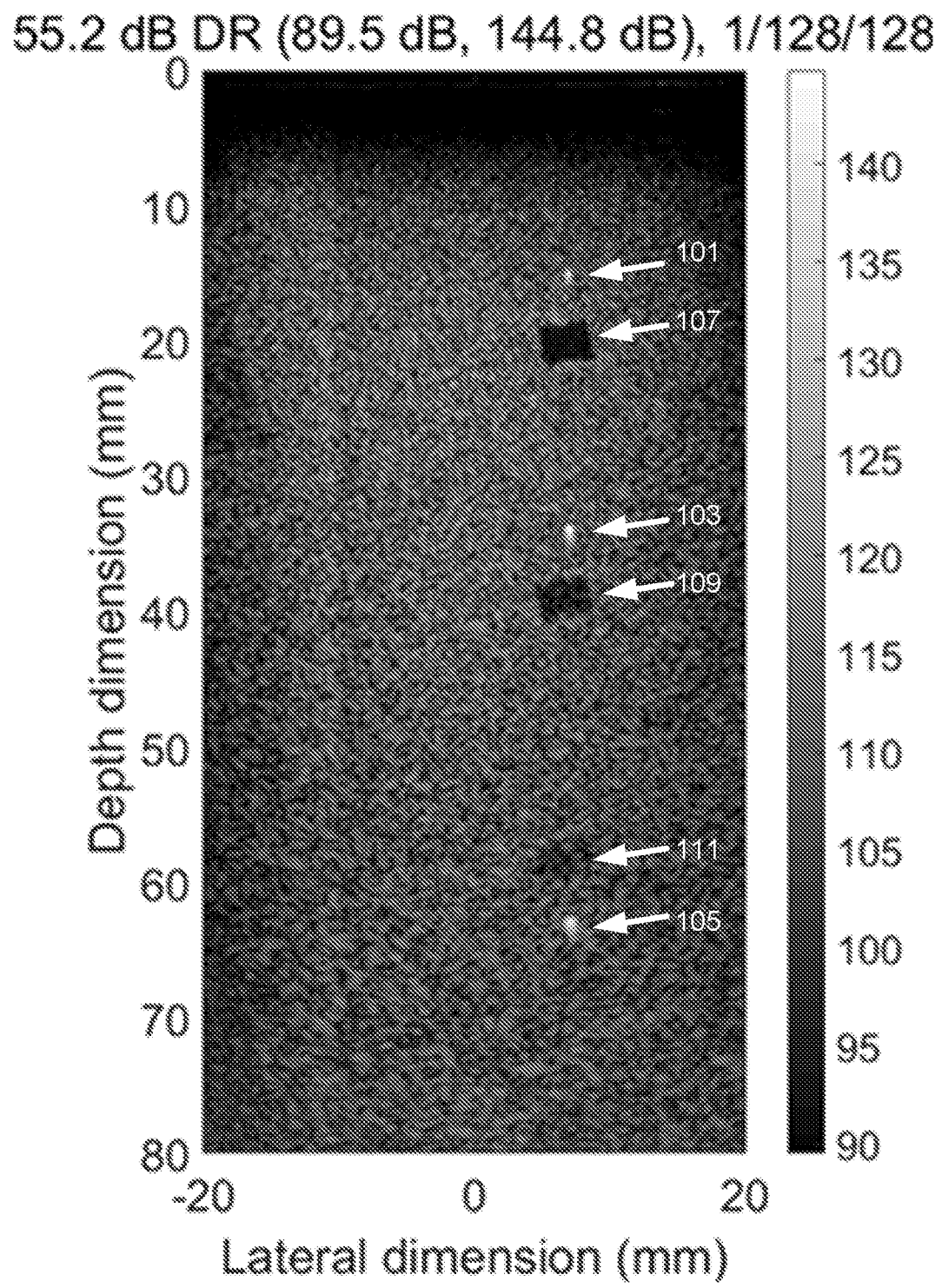
FIG. 1 shows an exemplary image obtained though full synthetic transmit aperture.

Acoustic imaging can be performed by emitting an acoustic waveform (e.g., pulse) within a physical elastic medium, such as a biological medium, including tissue. The acoustic waveform is transmitted from a transducer element (e.g., of an array of transducer elements) toward a target volume of interest (VOI). In conventional real aperture ultrasound imaging systems, the quality of images directly depends on the acoustic field generated by the transducer of the ultrasound system, and the image is typically acquired sequentially, one axial image line at a time (i.e., scan of the target area range slice by slice). This sets limits on the frame rate during imaging that may be detrimental in a variety of real-time ultrasound imaging applications, e.g., including the imaging of moving targets.

To address limitations with conventional real aperture ultrasound imaging, synthetic aperture ultrasound imaging can be used to improve the quality of ultrasound images. A "synthetic aperture" is the concept in which the successive use of one or more smaller, real apertures (sub-apertures) to examine a VOI, whose phase centers are moved along a known one-dimensional (1D), two-dimensional (2D), and/or three-dimensional (3D) path of a particular or arbitrary shape, is implemented to realize a larger effective (non-real) aperture for acquiring an image. The synthetic aperture can be formed by mechanically altering the spatial position of the electro-acoustic transducer (e.g., transducer array) to the successive beam transmission and/or receiving locations, by electronically altering the phase center of the successive beam transmission and/or receiving locations on the electro-acoustic transducer array, or by a combination of the above. Synthetic aperture-based imaging was originally used in radar systems to image large areas on the ground from aircraft scanning the area of interest from above. Synthetic aperture focusing in ultrasound imaging is based on the geometric distance from the ultrasound transmitting elements to the VOI location and the distance from that location back to the ultrasound receiving element. In ultrasound imaging, the use of the synthetic aperture enables the focusing on a point in the target region by analyzing the received amplitude and phase data of the returned echoes (e.g., mono-static and bi-static echoes), recorded at each of a plurality of transmitter and receiver positions from all directions, to provide information about the entire area. Since the direction of the returned echoes cannot be determined from one receiver channel alone, many receiver channels are used to determine the information contained in the returning echoes, which are processed across some or all of the channels to ultimately render information used to produce the image of the target region.

In some implementations of full synthetic transmit aperture imaging, each transmitter within the full set of transmitters can be excited sequentially, separately, in succession, consecutively, and individually. Echoes are recorded on the entire set of receivers for each transmitter spatial location. Considering a set of M transmitters and N receivers, which may or may not share spatial locations, the resulting number of ultrasound echoes equals M×N. For example, for a 128-element ultrasound array, the total number of echoes equals 16384. The echoes are fed into a delay-and-sum beamformer, which is applied to beamform a set of points in space comprising the image, and the resulting image is considered a "gold standard" for spatial resolution. The properties of full synthetic transmit aperture relate to the use of all available spatial samples (e.g., provided by transducer elements) on both transmission and reception combined with the virtual extension of the physical apertures due to the convolution of the transmit aperture with the receive aperture. In the case where the same aperture used for both transmit and receive, the effective aperture is double the size of the physical aperture, thus, decreasing the effective f-number and spatial resolution by a factor of two.

FIG. 1 shows an exemplary image 100 obtained though full synthetic transmit aperture. This example image is of a CIRS Model 044 ultrasound phantom and was obtained though full synthetic transmit aperture beamforming and has 55.2 dB of dynamic range, which was generated using a Philips/ATL L7-4 linear array operating at 5 MHz connected to a Verasonics ultrasound imaging system. The image depicts three 100 micrometer nylon wire targets (labeled 101, 103, 105), which are visible near 15 mm, 35 mm, and 65 mm depth, respectively. Likewise, the image shows four anechoic targets (labeled 107, 109, 111, and one not shown) are visible near 20 mm, 40 mm, 60 mm and 80 mm depth, respectively. The spatial resolution worsens with increasing depth due to the linearly increasing f-number with depth combined with defocusing of the elevation beam beyond approximately 30 mm.

It is well known to those knowledgeable in the field of synthetic aperture imaging that the majority of the spatial samples (e.g., transducer elements) corresponding to a given image point for full synthetic transmit aperture imaging may be redundant and/or may contain largely similar information. In fact, this redundancy is often exploited when the synthetic transmit aperture includes a reduced set of subapertures of two or more contiguous elements in order to improve SNR and speed acquisition, albeit with sacrifices in spatial resolution. Additionally, reduced-redundancy spatial sampling schemes are well known and readily formulated using products of k-space representations of transmit and receive apertures and corresponding transmit receive aperture response through linear convolution in the spatial domain.

An important redundancy in synthetic transmit aperture imaging is based on the principle of acoustic reciprocity, e.g., the echo resulting from transmission on element i and reception on element j is practically identical to the echo resulting from transmission on element j and reception on element i, by which approximately half of transmitter and receiver combinations are assumed to be identical. For example, with knowledge of Tx,Rx combination (i,j), Tx,Rx combination (j,i) may be recovered, assumed, and/or replaced. Moreover, it is well known that only 2N−1 out of $N^2$ echo samples, i.e., from all possible transmitter and receiver combinations for a given image point, are needed to form a nearly equivalent image. For example, from all Tx,Rx combinations (i,j), the required 2N−1 echo sample required for fully-spatially sampled image formation include combinations where i=j (corresponding to N echo samples) and combinations where i=j+1 (corresponding to N−1 echo samples) for a total of 2N−1 echo samples.

However, known techniques for using redundancy in synthetic transmit aperture imaging results in slow acquisition speeds due to the large number of transmits (N). Therefore, an opportunity exists to exploit redundancy in synthetic transmit aperture imaging to speed acquisition from N transmits to significantly less than N transmits.

Moreover, the process of transmitting on one element at a time is limited by the round-trip time, which is dictated by the sound speed and the depth-of-interest. Additionally, transmission on one element at a time greatly limits the amount of transmitted energy as compared to focused transmission using more than one element or other modes of coordinated transmission, including, but not limited to, plane wave transmission, virtual source transmission, and subaperture transmission. As such, full synthetic transmit aperture imaging suffers from poor SNR and penetration depth.

Coded aperture transmission greatly improves the amount of transmitted energy through the use of sets of orthogonal vectors that encode the transmit aperture. The Hadamard matrix can be used in coded aperture transmission based on a set of linearly independent vectors that is comprised solely of biphase values, −1 and 1. All Hadamard matrices are square with dimensions n×n, where n can be from the set 2k, and k is a non-negative integer. Many other values of n are also known to have Hadamard matrix properties. Let H be a Hadamard matrix of order n. The transpose of H is closely related to its inverse as follows:

$$HH^T = nI_n \qquad \text{Eq. (1)}$$

where $I_n$ is the n×n identity matrix and $H^T$ is the transpose of H. Equation (1) is due to the fact that the rows and columns of H are all orthogonal vectors over the field of real numbers and each vector has length of $\sqrt{n}$ (i.e., square root of n). Equation (1) shows that the Hadamard matrix enables perfect separation of all channels provided that each row vector of the Hadamard spatial code is time invariant with respect to all other row or column vectors. Thus, for an aperture having N transmitters and N receivers, the SNR improvement based on Hadamard spatial encoding is given by $\sqrt{N}$ due to the fact that N transmitters are active versus only 1.

Typically, the transducer array is excited using the orthogonal vectors of the Hadamard matrix in the case of a bipolar transmitter (−1, 1); or, the transducer array can be excited using the related binary version of the Hadamard matrix, e.g., the S-matrix (scattering matrix), in the case of a unipolar binary transmitter (0, 1). Although the S-matrix has minor limitations that make it slightly inferior to the Hadamard matrix, it is useful in some applications, for example, when the transmitter output cannot be inverted.

The Hadamard matrix enables a zero-delay spatial phase encoding scheme. Thus, the spatial encoding and decoding process assumes that there is inconsequential delay between transmissions of orthogonal vectors. In other words, acoustic echoes are decoded assuming no motion or change occurs between transmissions, and assuming that the only variable between transmissions is the specific row (or column) of H being transmitted. The decoding is independent of the delay-and-sum operation in the beamformer. The method also assumes that the elements of each orthogonal vector are transmitted simultaneously with ideal timing such that there is no delay between transmissions comprising each orthogonal vector. The set of acoustic echoes corresponding to the orthogonal vectors of the Hadamard matrix are thus decoded simultaneously, assuming zero delay or phase between rows or columns or between any elements of the Hadamard matrix.

One primary disadvantage that the Hadamard encoding scheme shares with full synthetic transmit aperture transmission is that it requires n transmissions, which limits the true refresh rate to the pulse repetition frequency (PRF) divided by n. The apparent refresh rate is equal to the PRF when the echo set corresponding to the last transmitted Hadamard orthogonal vector is replaced prior to beamformation; however, the complete and proper sampling of motion is limited by the PRF/n, thus resulting in motion blur artifacts for velocities on the order of 1 wavelength times the PRF/n. Another disadvantage of Hadamard spatial encoding is that it is limited to square matrices of specific sizes. Another disadvantage of Hadamard spatial encoding is that it does not utilize temporal coding in order to reduce the acquisition time of the entire set.

Hadamard spatial encoding has also been extended to the use of complementary coded waveforms, e.g., Golay coded waveforms, for additional SNR improvement. Nonetheless, the fundamental operation and associated limitations primarily follows that of Hadamard spatial encoding.

Hadamard spatial encoding has also been extended to the use of delay encoded transmission instead of phase encoding, albeit with significantly greater decoding complexity. Nonetheless, the fundamental operation and associated limitations primarily follows that of Hadamard spatial encoding.

To achieve the best possible imaging speed and resolution, all spatial frequencies must be excited simultaneously or nearly simultaneously in order to mitigate effects of time variance, e.g., tissue motion. Hadamard spatial encoding excites all spatial frequencies, but they are not all excited simultaneously. Only when the linear combination of the entire set of orthogonal vectors is considered (e.g., see Eq. (1)) are all spatial frequencies excited. This is evidenced by the fact that the Fourier transform of the Hadamard matrix is not a constant value for each transmit vector as illustrated in FIG. 2B for the Hadamard matrix shown in FIG. 2A—the transmit vectors are in each row.

Figure 2B:
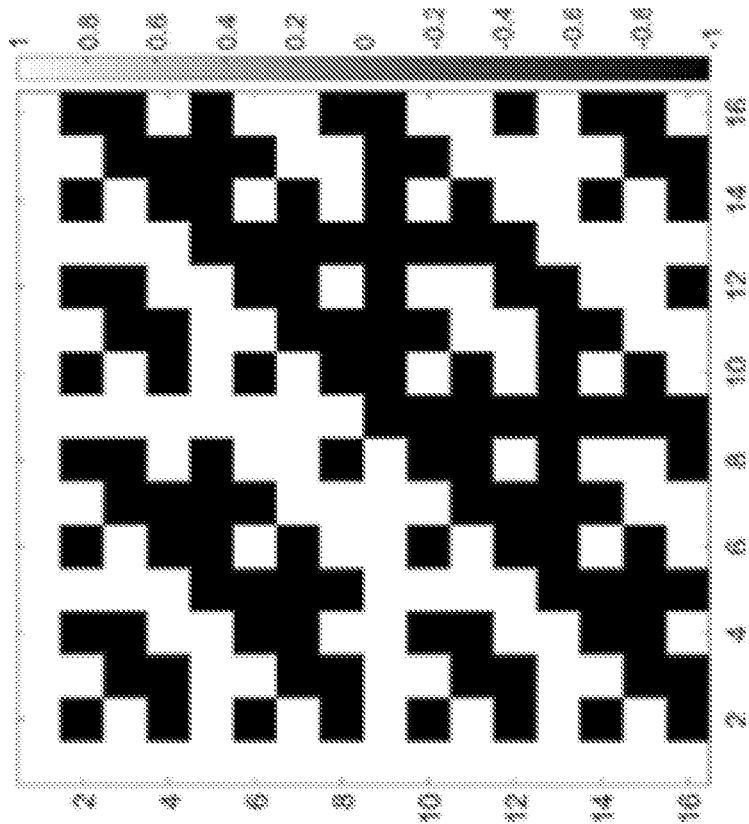
FIG. 2B shows an exemplary diagram for magnitude of the discrete Fourier transform of n=16 Hadamard matrix rows, shown in FIG. 2A, with DC value being leftmost in each row.
Figure 2A:
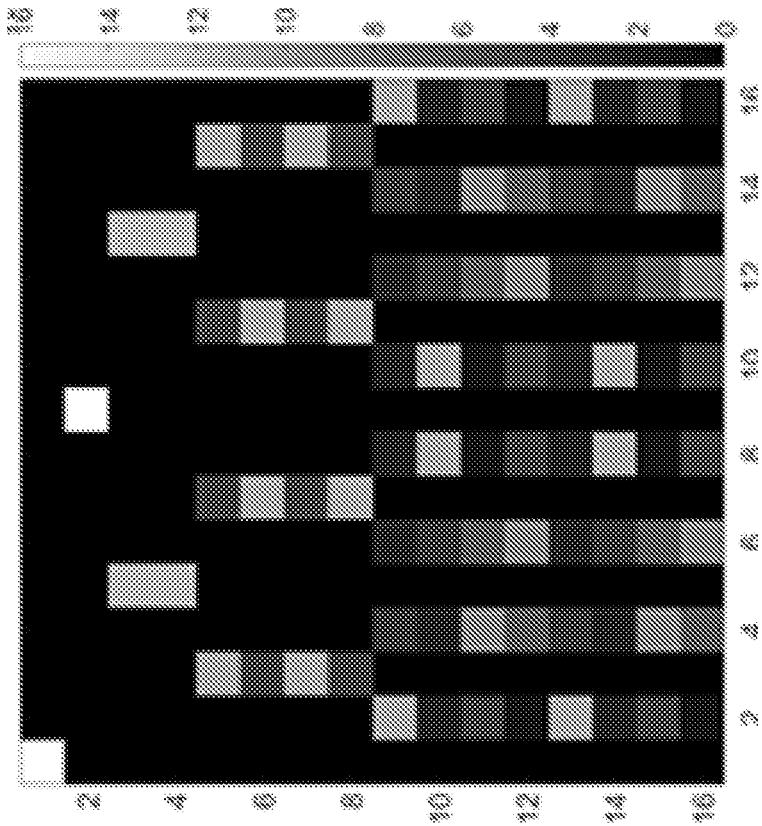
FIG. 2A shows an exemplary Hadamard matrix diagram corresponding to n=16 with transmit vectors in each row.

FIGS. 2A and 2B show diagrams of an example Hadamard matrix corresponding to n=16 with transmit vectors in each row (FIG. 2A) and of the discrete Fourier transform for the n=16 Hadamard matrix rows from FIG. 2A with DC value being leftmost in each row (FIG. 2B). For example, as the entire set must be transmitted in order to recover all spatial frequencies, Hadamard spatial encoding is very susceptible to motion artifacts.

An encoding strategy that is less susceptible to motion would utilize a spatial encoding scheme that excites all spatial frequencies equally for each transmit vector. Other spatial encoding schemes may be realized that have perfect linear separation similar to Equation (1) with the additional constraint that all spatial frequencies are excited simultaneously. Such strategy may still be subject to the limitation of N transmits, but the redundancy of spatial sampling information will guarantee less susceptibility to motion.

Disclosed are techniques, systems, and devices for spatial and temporal encoding of transmission in full synthetic transmit aperture imaging to achieve spatial and contrast resolution for medical imaging with fewer signal transmissions.

In some example embodiments, a probe device includes one or more transducer segments including an array of transducer elements, and a probe controller in communication with the array of transducer elements to select a first subset of transducer elements of the array to transmit waveforms, and to select a second subset of transducer elements of the array to receive returned waveforms, wherein the first subset of transducer elements are arranged to transmit the waveforms toward a target volume in a biological subject and the second subset of transducer elements are arranged to receive the returned waveforms that return from at least part of the target volume. The probe device is operable to transmit, at the target volume, spatially and temporally encoded waveforms that include a predetermined (i) unique set of waveforms, (ii) transmit delay pattern, and/or (iii) transmit amplitude and phase pattern; such that, after receiving returned acoustic waveforms from the target, the returned waveforms are decoded by processing waveform components corresponding to each transmit transducer element are separated from the waveforms on each receive transducer element resulting in a set of waveforms representative of a full synthetic transmit aperture acquisition.

In some example embodiments, a method for encoding acoustic signal transmissions is disclosed. The method comprises transmitting by a first transducer element, after a time delay associated with the first transducer element, waveforms towards a target volume in a biological subject; receiving by a second transducer element, after a round-trip time between the first transducer element and the second transducer element, returned waveforms that return from at least part of the target volume; identifying the first transducer element that contributes to the returned acoustic waveforms based on the time delay and the round-trip time; and processing the returned waveforms based on the identification of the first transducer element to generate an image of the target volume in the biological subject.

Figure 3:
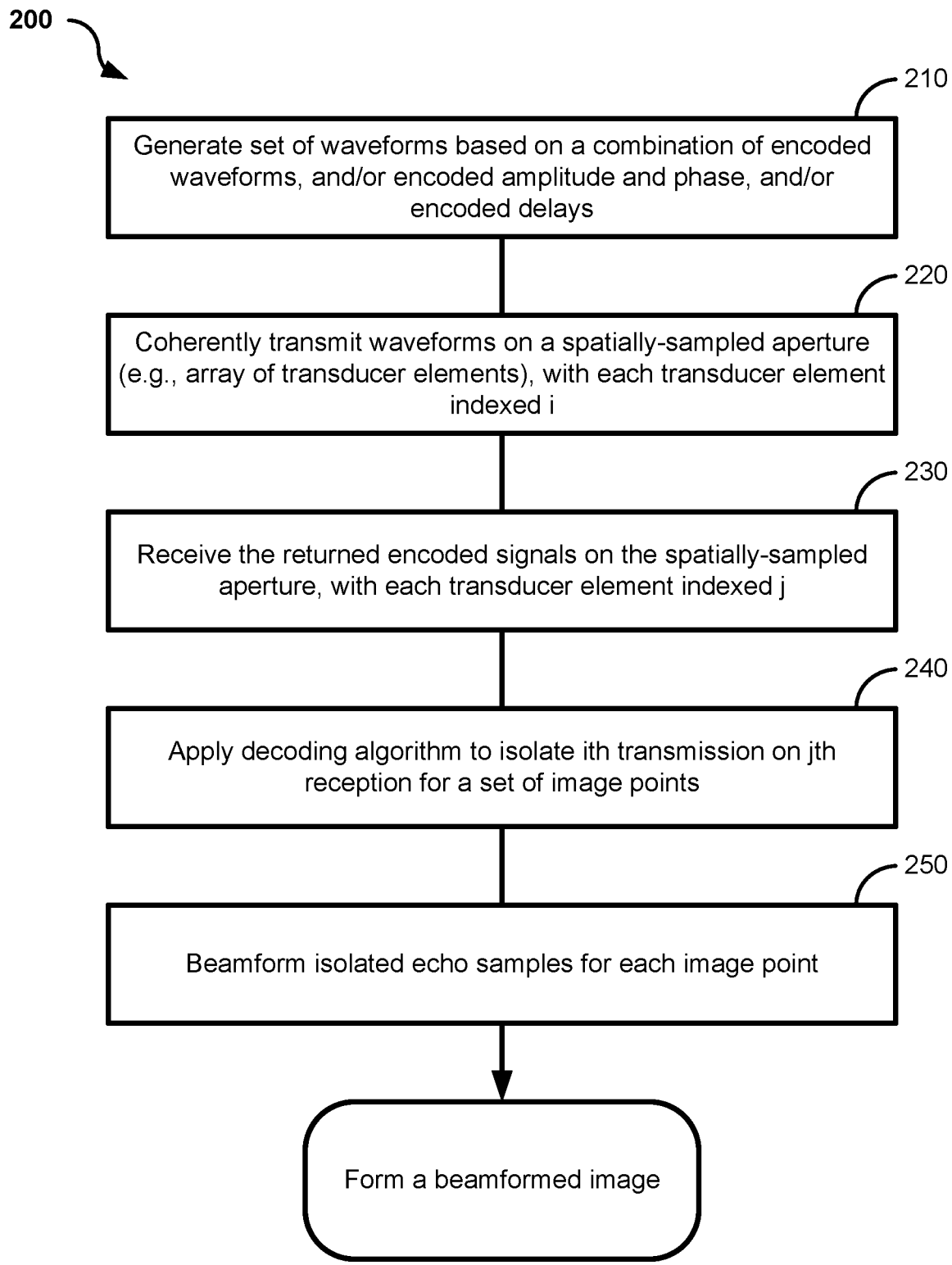
FIG. 3 shows a diagram of an example method for spatial and temporal encoding and decoding of acoustic waveforms in synthetic aperture acoustic imaging in accordance with the disclosed technology.

FIG. 3 shows a diagram of an example embodiment of a method 200 for spatial and temporal encoding of acoustic waveforms in synthetic aperture acoustic imaging in accordance with the disclosed technology. The method 200 includes a process 210 to generate a set of spatially and temporally encoded acoustic waveforms for transmission toward a target volume, in which the encoding includes generating one or more of (i) a unique set of encoded waveforms, (ii) a pattern for the transmit delay of the waveforms of the set of waveforms to be transmitted at the target volume, and/or (iii) a transmit amplitude and phase pattern of the set of waveforms to be transmitted at the target volume. The method 200 includes a process 220 to coherently transmit waveforms, toward the target volume, on a spatially-sampled aperture formed on an array of transducer elements for one or more transducer segments of an acoustic probe device, in which each transducer element is indexed (e.g., 1, 2, ... i). The method 200 includes a process 230 to receive the returned acoustic waveforms, which are based on the transmitted encoded acoustic signals, on the spatially-sampled aperture, in which each transducer element is indexed j (e.g., 1, 2 . . . j). The method 200 includes a process 240 to decode the returned (encoded) acoustic waveforms to isolate the $i^{th}$ transmission on the $j^{th}$ reception for a set of image points of the target volume. Some example implementations of the decoding process 240 includes the method 240, described later with respect to FIG. 24. The method 200 includes a process 250 to beamform isolated echo samples for each image point of the set of image points of the target volume, to produce a data set that can be processed to form a beamformed image of the target volume.

In some implementations of the method 200, the process 210 includes generating a set of encoded waveforms for transmission. In such implementations, these encoded waveforms are derived from codes, i.e., sets of numbers, with specific properties. For example, a useful property of an encoded waveform is that when decoded, the range lobes are small or close to zero and the amplitude of the decoded waveform is higher than the encoded waveform. The decoding process, for this example, could include range compression or matched filtering. Another example property of two or more encoded waveforms is that the two or more encoded waveforms are orthogonal. For example, given a set of two encoded waveforms, if the first waveform is decoded with the decoding method for the second waveform, the output is ideally zero. Likewise, if the second waveform is decoded with the decoding method for the first waveform, the output is ideally zero. Likewise, the orthogonality obeys linearity and time invariance, e.g., a composite waveform formed from a linear combination of the first and second waveforms through operations including scaling, addition, subtraction, and/or delay may be decoded. Preferably, a unique set of encoded waveforms generated by the process 201 includes two or more encoded waveforms that are both ideally compressive and ideally orthogonal. Sets of these waveforms may include waveforms that are frequency-coded and/or phase-coded, but such frequency-coding and/or phase-coding are optional, and the unique set of encoded waveforms can include arbitrary waveforms that simultaneously satisfy the properties of range compression and orthogonality. In practice, it is difficult to achieve both properties simultaneously and ideally for more than two waveforms, and thus, tradeoffs must be made. The non-ideal nature of the range compression and/or orthogonality can be reduced by including spatial delay and/or spatial amplitude and phase encoding, in which these techniques can be included in implementations of the process 210.

Figure 4:
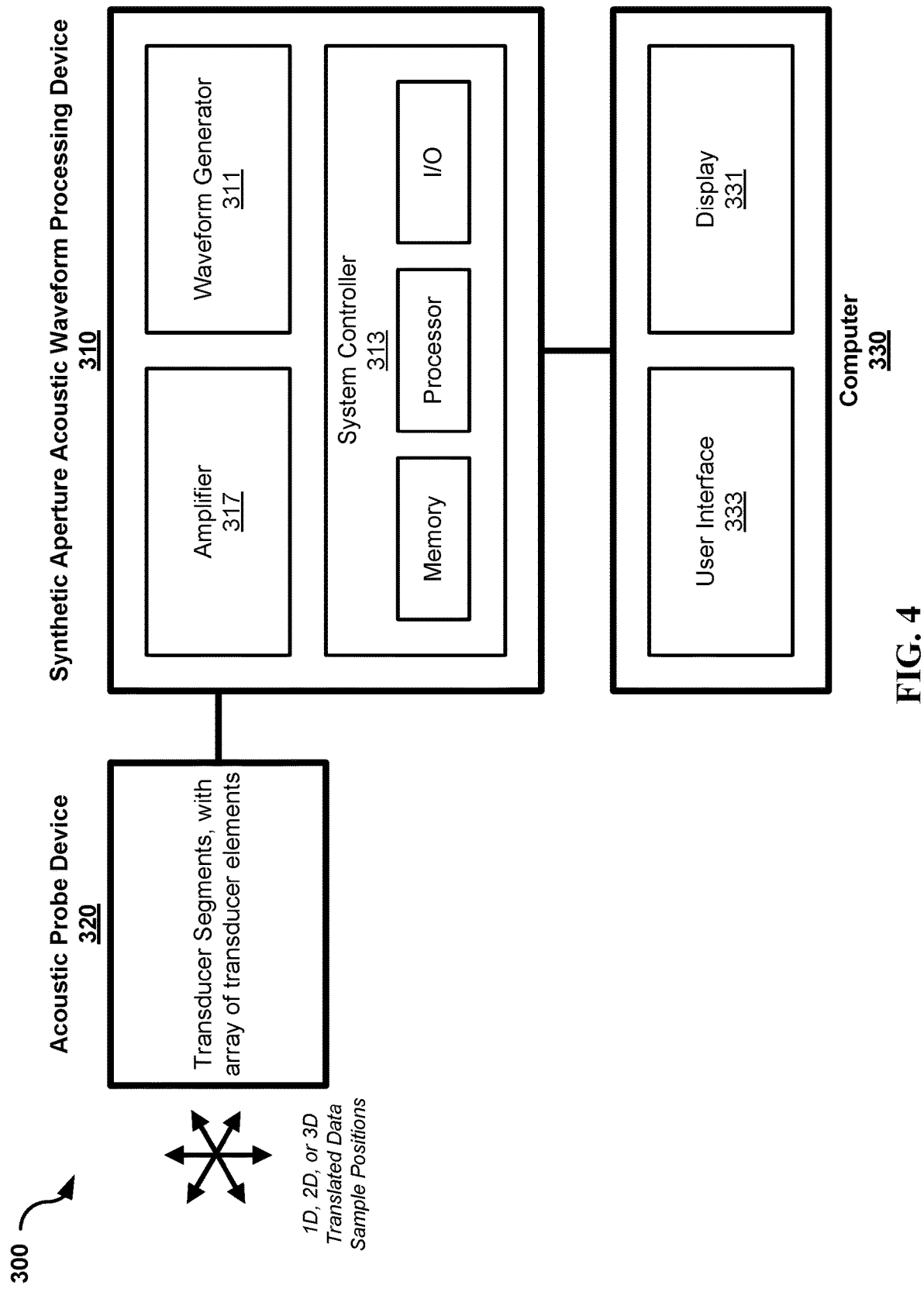
FIG. 4 shows a diagram of an example embodiment of a system for spatial and temporal encoding of acoustic waveforms in synthetic aperture acoustic imaging in accordance with the disclosed technology.

FIG. 4 shows a diagram of an example embodiment of a system 300 for spatial and temporal encoding of acoustic waveforms in full synthetic transmit aperture acoustic imaging. The system 300 is operable to implement the method 200 for spatially and temporally encoding transmit waveforms and decoding the returned encoded waveforms to produce a beamformed image. In some implementations, the system 300 is operable to generate spatially and temporally encoded waveforms in the form of composite acoustic waveforms that include a spread-spectrum, wide instantaneous bandwidth, coherent, pseudo-random noise characteristics, and coding. The example system 300 illustrates one of many system designs in accordance with the disclosed technology.

As shown in the example of FIG. 4, the system 300 includes a synthetic aperture acoustic waveform (SAAW) processing device 310 and an acoustic probe device 320 in communication with the SAAW processing device 310. The system 300 includes a computer 330, in communication with the SAAW processing device 310, that includes a processing unit (not shown), a display 331 and user interface module 333 to receive data input and display data output for operation of the system 300. The computer 330 can be implemented as one of various data processing architectures, such as a personal computer (PC), laptop, tablet, and mobile communication device architectures. In some examples, the user interface 333 can include many suitable interfaces including various types of keyboard, mouse, voice command, touch pad, and brain-machine interface apparatuses.

The SAAW processing device 310 includes a system controller 313 comprising a data processing unit. The data processing unit of the system controller 313 includes a processor to process data, a memory in communication with the processor to store data, and an input/output unit (I/O) to interface the processor and/or memory to other modules, units or devices of the electronics unit, or external devices. For example, the processor can include a central processing unit (CPU), a microcontroller unit (MCU), or other processor units. For example, the processor can include ASIC (application-specific integrated circuit), FPGA (field-programmable gate array), DSP (digital signal processor), AsAP (asynchronous array of simple processors), and other types of data processing architectures. For example, the memory can include and store processor-executable code, which when executed by the processor, configures the data processing unit to perform various operations, e.g., such as receiving information, commands, and/or data, processing information and data, transmitting or providing information/data to the acoustic probe device 320 and/or computer 330. In some implementations, the data processing unit of the system controller 313 (and/or the processing unit of the computer 330) can transmit raw and/or processed data to a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory. The I/O of the data processing unit of the system controller 313 (and/or the processing unit of the computer 330) can interface the data processing unit with the wireless communications unit to utilize various types of wired or wireless interfaces compatible with typical data communication standards, for example, which can be used in communications of the data processing unit with other devices, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor, stored in the memory, or exhibited on an output unit or an external device.

The SAAW processing device 310 includes a waveform generator 311, which can be controlled by the system controller 313, to produce one or more digital waveforms in accordance with the disclosed spatially and temporally encoded synthetic acoustic transmit aperture techniques. The waveform generator 311 includes an array of waveform synthesizers and beam controllers, which generate analog electronic signals corresponding to the one or more digital waveforms that the acoustic probe device transduces as acoustic waveforms, e.g., including the spatially and temporally encoded composite acoustic waveform. The waveform generator 311 can include a function generator or an arbitrary waveform generator (AWG). For example, the waveform generator 311 can be configured as an AWG to generate arbitrary digital waveforms for the waveform synthesizer and beam controller to synthesize as individual analog waveforms and/or a composite analog waveform. In some implementations, the waveform generator 311 can include a memory unit that can store pre-stored waveforms and coefficient data and information used in the generation of a digital waveform.

In some implementations, the waveform synthesizer and beam controller of the waveform generator 311 includes I number of array elements. In one example, the waveform synthesizer and beam controller can be configured to include at least one waveform synthesizer element on each line of the I number of array waveform synthesizers. In another example, the waveform synthesizer and beam controller can include at least one beam controller element on each line of the I number of array beam controllers. In another example, the waveform synthesizer and beam controller can include at least one waveform synthesizer element and beam controller element on each line of the I number of array waveform synthesizers and beam controllers. The waveform synthesizer and beam controller can include a phase-lock loop system for generation of an electronic signal, e.g., a radio frequency (RF) waveform. An exemplary RF waveform can be synthesized by the waveform synthesizer and beam controller from individual waveforms generated in the array elements of the waveform synthesizer and beam controller, e.g., one individual RF waveform can be generated in one array element substantially simultaneously to all other individual waveforms generated by the other array elements of the waveform synthesizer and beam controller. Each individual orthogonal RF waveform can be defined for a particular frequency band, also referred to as a frequency component or 'chip', and the waveform properties of each individual orthogonal waveform can be determined by the waveform generator 311, which can include at least one amplitude value and at least one phase value corresponding to the chip. The waveform generator 311 can issue commands and send waveform data including information about each individual orthogonal waveform's properties to the waveform synthesizer and beam controller for generation of individual orthogonal RF waveforms that may be combined together to form a composite RF waveform by the waveform synthesizer and beam controller.

In some embodiments, the SAAW processing device 310 includes an amplifier 317 to modify the generated waveforms produced at the waveform generator 311, e.g., the individual orthogonal RF waveforms and/or the composite RF waveform generated by the waveform synthesizer and beam controller. For example, the amplifier 317 can include an array of I number of amplifiers, each operable to amplify the gain and/or shifting the phase of a waveform. In some examples, the array of amplifiers is configured as linear amplifiers. While the amplifier 317 is shown as part of the SAAW processing device 310, the amplifier 317 can also or alternatively be included in the acoustic probe device 320.

In some embodiments, the system controller 313 can control some or all of the modules of the system 300, e.g., through connection via a control bus. In some embodiments, the system controller 313 includes a master clock for time synchronization. For example, the master clock can interface with the system controller 313 and other modules of the system 300 synchronize operations with each other. In various implementations, for example, the SAAW processing device 310 is operable to implement the processes 210, 220, 230, 240 and/or 250 of the method 200. In various implementations, for example, the acoustic probe device 320 is operable to implement the processes 220 and/or 230 of the method 200 in conjunction with the SAAW processing device 310.

The acoustic probe device 320 includes one or more transducer segments that can include an array of transducer elements. The acoustic probe device 320 includes a probe controller in communication with the one or more transducer segments (e.g., in communication with the array of transducer elements) to select a first subset of transducer elements of the array to transmit waveforms, and to select a second subset of transducer elements of the array to receive returned waveforms. In some implementations, the first subset of transducer elements are arranged to transmit the waveforms toward a target volume in a biological subject (e.g., living organism) and the second subset of transducer elements are arranged to receive the returned waveforms that return from at least part of the target volume, and the waveforms are transmitted in accordance with a predetermined transmit delay pattern such that each of the returned waveforms is distinguishable.

In some examples, a transduced acoustic wave can be emitted in the form of an acoustic waveform burst. For example, a selected array element of the example transducer array (of a transducer segment) may generate (e.g., transduce) two or more individual orthogonal acoustic waveforms that correspond to the individual orthogonal waveforms determined by the waveform generator 311 and combined spatially to form a composite acoustic waveform. As an example, a selected array element may generate (e.g., transduce) one or more composite acoustic waveforms that correspond to the composite waveforms determined by the waveform generator 311.

In some embodiments, for example, the acoustic probe device 320 includes a transmit/receive (T/R) switch configured to allow the acoustic probe to utilize the same transducer element(s) in both a transmit and a receive mode. For example, in transmit mode, the exemplary transduced and transmitted spatially and temporally encoded composite acoustic waveform can be transmitted toward a target area from a plurality of positions of the transducer array relative to the target, e.g., biological tissue, in which the transduced and transmitted acoustic waveform forms a spatially combined acoustic waveform. The transmitted spatially and temporally encoded composite acoustic waveform can propagate into the target medium, which for example, can have one or more inhomogeneous mediums that partially transmit and partially reflect the transmitted acoustic waveform. For example, after the acoustic waveform has been transmitted, the T/R switch can be configured into receive mode. The exemplary composite acoustic waveforms that are (at least partially) reflected by the target can be received by the transducer array, e.g., returned spatially and temporally encoded acoustic waveforms. In some examples, a returned acoustic waveform corresponding to the individual orthogonal waveforms (e.g., frequency chips) can be converted to an analog RF waveform. In some examples, selected transducer elements can be configured to receive the returned acoustic waveform(s) corresponding to the transmitted composite waveform and convert it to a composite analog RF waveform.

In some implementations, for example, the probe device 320 can have the beam phase center(s) mechanically translated in one dimension, two dimensions, and/or three dimensions of data sampling/ultrasound scanning positions by spatially moving the transducer array (of the one or more transducer segments) to produce a synthetic aperture during an ultrasound imaging implementation using the system 300. Additionally or alternative, in some implementations, for example, the probe device 320 can remain stationary, and the beam phase center(s) may be translated electronically in one dimension, two dimensions, and/or three dimensions along the stationary transducer array (of the one or more transducer segments) by individually addressing transducer elements sequentially or randomly, e.g., based on control signals from the system controller 313, as data sampling/ultrasound scanning positions to produce a synthetic aperture during an ultrasound imaging implementation using the system 300. For example, the system 300 can both mechanically and electronically translate the phase centers in one dimension, two dimensions, and/or three dimensions of data sampling/ultrasound scanning positions to produce a synthetic aperture during an ultrasound imaging implementation. An example embodiment of the one or more transducer segments of the acoustic probe device 320 is discussed later with respect to FIGS. 12 and 13.

The disclosed techniques, systems, and devices present an alternative solution from zero-delay spatial encoding/decoding techniques. The disclosed technology includes a technique for spatially and temporally encoding coherent transmissions on a plurality of ultrasound transducers to achieve partial or full synthetic transmit aperture imaging with fewer transmits than are required of other coded aperture schemes while still maintaining similar spatial resolution and contrast resolution.

Consider a transmit aperture that is encoded in waveform, amplitude and phase, and/or delay, and the corresponding acoustic echoes are decoded for each point in space. Using the disclosed technique, each acoustic sample corresponding to a point in space relates to a specific combination of transmitter and receiver that is unique according to its waveform, amplitude and phase, and/or delay, such that when decoded, full synthetic transmit aperture delay-and-sum beamformation results. The disclosed technique is markedly different than spatial Hadamard-based schemes, where the decoding happens across sets of echo samples with the exact same delay across the receive aperture and across orthogonal transmit vectors, independent of image formation.

Considering the case of infinite transmit bandwidth and a set of point transmitters, a set of transmission events may overlap a single point in space for only very specific situations. For example, a set of transmit events such that they are all delayed to arrive simultaneously at the same point in space, e.g., geometric focusing to a point. For no other points in space do all transmissions arrive simultaneously aside from well-known spatial sampling conditions that result in aliasing. The echoes from all other locations in space except for the focal point may coincide with one or more transmissions, but they do not overlap or constructively interfere completely. Imaging is amplified at the focal point, and there is no distinction as to which transmitter contributes to which echo sample in a particular receiver.

In contrast, for the same impulse and point source transmit situation, the set of transmissions may occur with a unique delay pattern such that the echoes received from a point target in space coincide to the individual transmitters when the received echoes are delayed according to the unique set of delays associated with the transmitters in implementations in accordance with the disclosed techniques. Echoes generated from targets may be considered independent point sources of sound impulses, each arriving at the array of receivers with unique delays according to the unique transmitter delays. All points in space are treated equally, thus enabling imaging of the whole target space, and there is separation of which transmitter contributes to which echo sample in a particular receiver based on the unique combination of transmit delay and round-trip time for a particular combination of transmitter and receiver, thus, all spatial frequencies are excited and potentially recoverable.

In some embodiments, transmissions occur on a plurality of transducer elements according to a set of random time delays. Here, the term "random" refers to a set of computer-generated pseudo-random numbers, also referred to herein as random numbers. The random numbers may be generated according to probability distributions including, but not limited to uniform, normal (Gaussian), Cauchy, exponential, and/or chi-squared. Sets of random numbers may be statistically independent, i.e., the sets are statistically uncorrelated. Some sets of random numbers may function better than others, thus choosing, manipulating, and/or optimizing sets of random numbers or sets seeded by random numbers can facilitate a better outcome.

Due to the random nature of the transmit delays combined with finite temporal bandwidth and finite spatial bandwidth, unwanted overlap of transmit and receive events coincident with a point in space poses a problem for the method considering a single set of random transmit delays. Considering multiple transmissions of multiple random sets of time delays, for example, the overlapping echoes will occur randomly, and thus, echo samples will be uncorrelated across multiple sets, and thus, more easily rejected in a delay-and-sum beamformer. As each set is statistically independent of the former, the SNR improves monotonically as the number of transmissions tends towards infinity. In a practical application, for example, the number of transmissions cannot be infinity; however, the SNR improves with the square root of the number of independent transmissions.

The set of random time delays may be chosen from a uniform random distribution of real numbers spanning a range of delays, for example, spanning real numbers ranging from 0 to 200 wavelengths. The range of delays is primarily limited by transmit to receive crosstalk during transmission, and the corresponding maximum tolerated standoff distance determined by the maximum delay, e.g. 200 wavelengths as in the previous example. Multiple sets of delay values randomly sampled from the same range include a sequence of transmissions that fire sequentially at a specified PRF. The range of delays preferably span from 0 to the maximum tolerated standoff distance.

Example implementations of the disclosed spatial and temporal encoding techniques are described below, including example results using various encoded delays. In the example implementations, the array geometry may be suitably optimized to accommodate the required standoff distance, e.g., optimization of the focal distance in elevation for a 1-D linear array geometry.

Figures 5A, 5B:
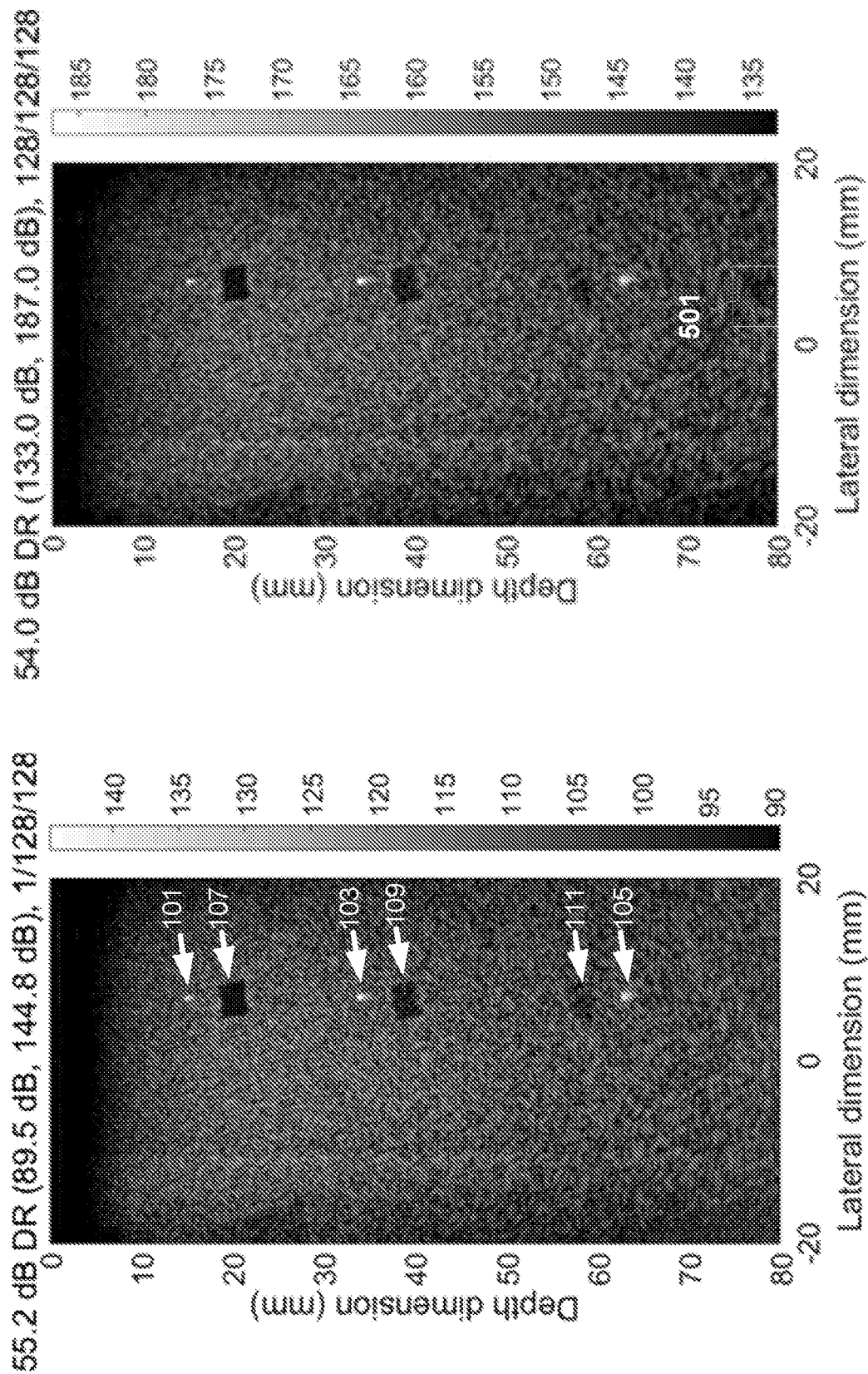
FIGS. 5A and 5B show, respectively, exemplary images obtained through full synthetic transmit aperture and delay encoded synthetic transmit aperture for 128 sets of 128 delays.

FIGS. 5A and 5B show, respectively, exemplary images obtained through full synthetic transmit aperture and delay encoded synthetic transmit aperture for 128 sets of 128 delays. FIG. 5A shows the same image shown in FIG. 1, which is provided here in FIG. 5A for comparative purposes with the image shown in FIG. 5B. As previously discussed, FIG. 1 shows an example of a full synthetic transmit aperture image captured with 55.2 dB of dynamic range for comparison.

FIG. 5B shows an example image demonstrating a delay encoded synthetic transmit aperture for 128 sets of 128 delays. The example delay encoded synthetic transmit aperture image shown in FIG. 5B is also of the example CIRS model 044 ultrasound phantom, which was generated using a Philips/ATL L7-5 linear array operating at 5 MHz connected to a Verasonics ultrasound imaging system. The image displays 54.0 dB of dynamic range. The image is the result of coherent summation over 128 sets of random delay encoding vectors spanning 0 to 30 wavelengths. There is slightly reduced contrast in the top anechoic lesion in the top image as compared to FIG. 5A and artifacts above and below each of the three wire targets. Notably, for example, there are some similarities between the images due to equivalent spatial sampling. The top-end range of the absolute image brightness level of 187.0 dB is much greater as compared to 144.8 dB. Also, the noise-free depth-of-penetration is much improved for the delay encoded image, thus revealing the anechoic target (shown in box labeled 501) at 80 mm depth, which is not shown in FIG. 5A.

Figures 6A, 6B:
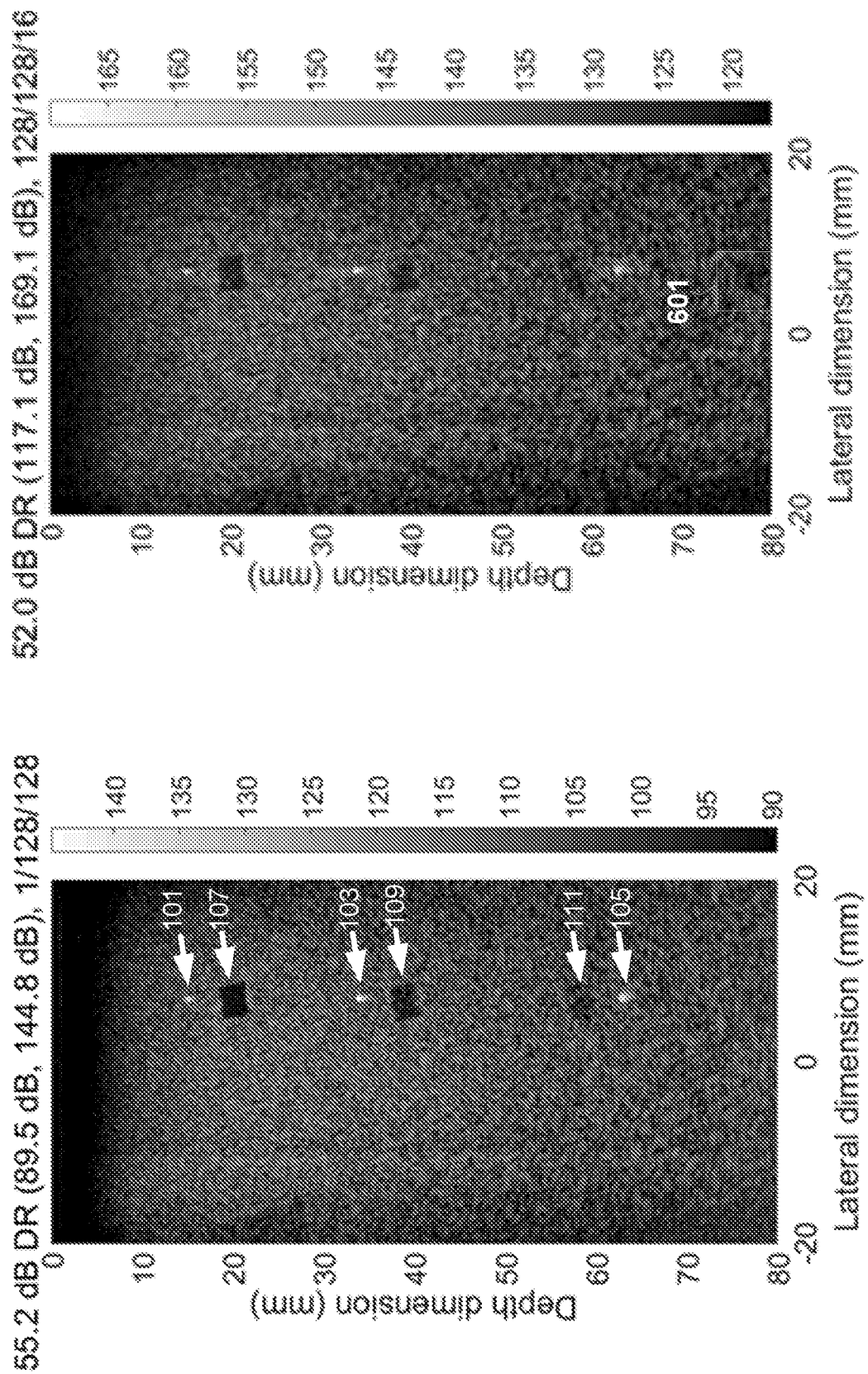
FIGS. 6A and 6B show, respectively, exemplary images obtained through full synthetic transmit aperture and delay encoded synthetic transmit aperture for 16 sets of 128 delays.

FIGS. 6A and 6B show, respectively, exemplary images obtained through full synthetic transmit aperture and delay encoded synthetic transmit aperture for 16 sets of 128 delays. FIG. 6A again shows the full synthetic transmit aperture image (i.e., same as FIG. 1) captured with 55.2 dB of dynamic range for comparison with FIG. 6B. FIG. 6B shows the delay encoded synthetic transmit aperture image of the example CIRS model 044 ultrasound phantom generated using a Philips/ATL L7-5 linear array operating at 5 MHz connected to a Verasonics ultrasound imaging system. In the image of FIG. 6B, 52.0 dB of dynamic range is displayed. The image of FIG. 6B is the result of coherent summation over 16 sets of random delay encoding vectors spanning 0 to 30 wavelengths (e.g., compared to 128 delay sets in FIG. 5B). As shown in the image, for example, there is reduced contrast in all lesions due to overlapping echoes, though spatial information is largely preserved despite no optimization of the random delay pattern. The noise-free depth-of-penetration is still much improved for the delay encoded image, as compared to FIG. 6A for example, showing the anechoic target (shown in box labeled 601) at 80 mm depth, albeit with 8× the frame rate speed.

Figure 7B:
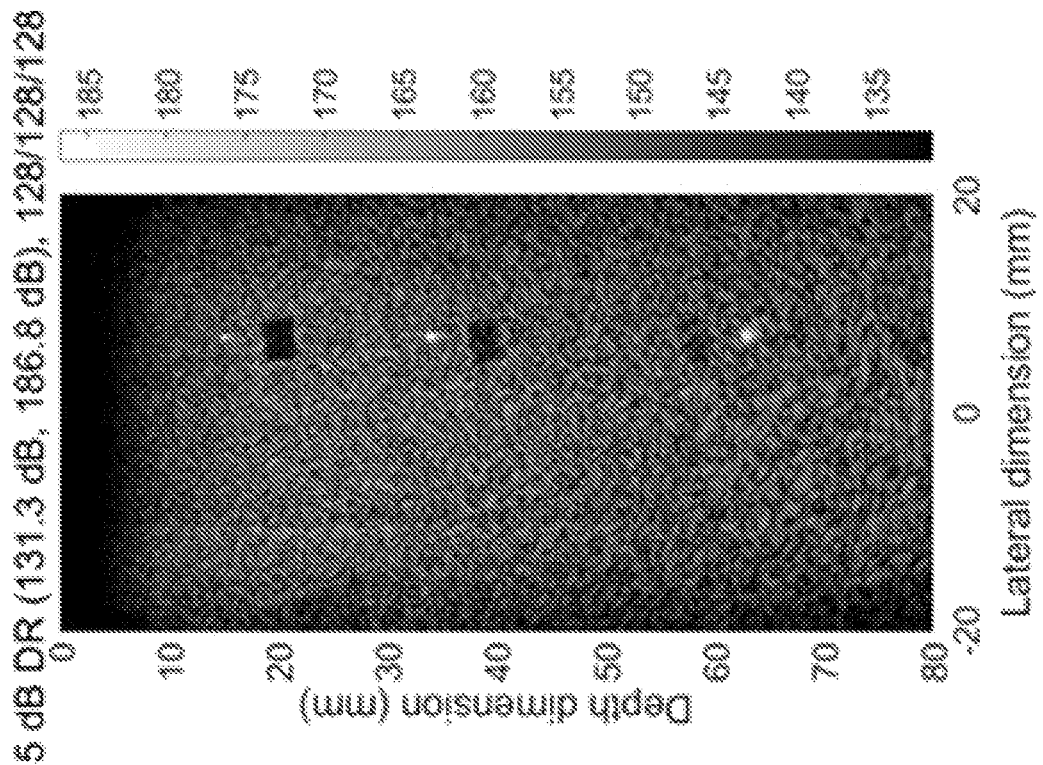
FIGS. 7A and 7B show, respectively, exemplary images obtained through full synthetic transmit aperture and delay encoded synthetic transmit aperture for 128 sets of delays spanning 0 to 1 wavelength.
Figure 7A:
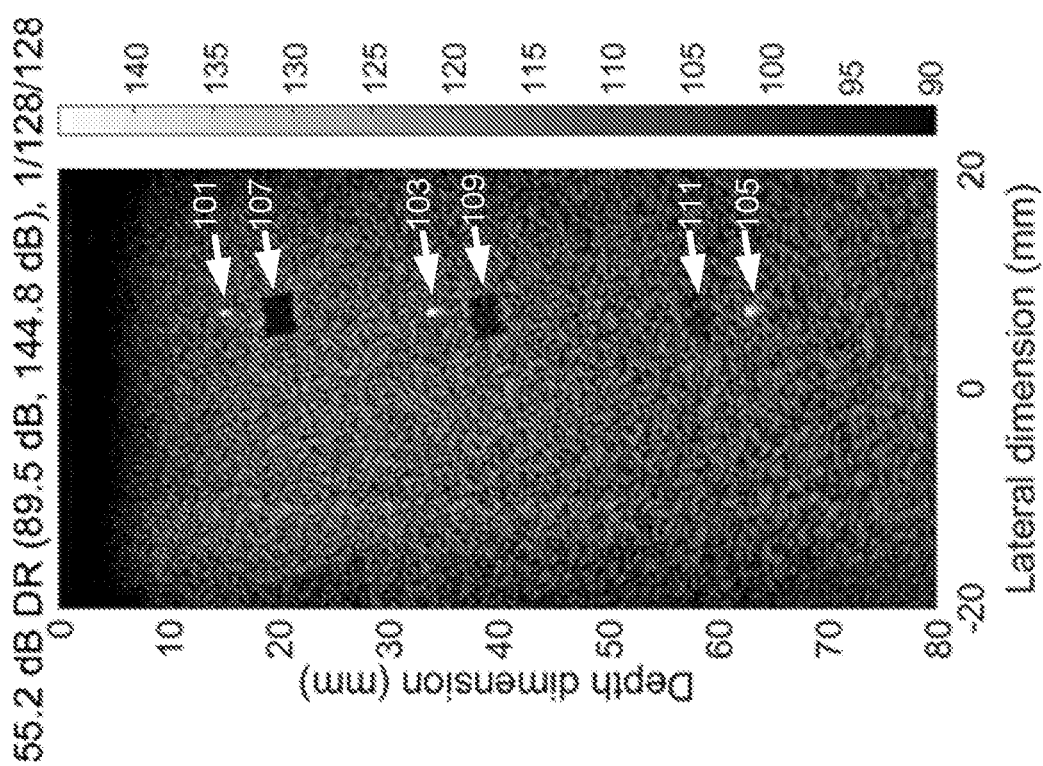

FIGS. 7A and 7B show, respectively, exemplary images obtained through full synthetic transmit aperture and delay encoded synthetic transmit aperture for 128 sets of delays spanning 0 to 1 wavelength. FIG. 7A shows the full synthetic transmit aperture image (same as FIG. 1) captured with 55.2 dB of dynamic range for comparison. FIG. 7B shows the delay encoded synthetic transmit aperture image of the example CIRS model 044 ultrasound phantom generated using a Philips/ATL L7-5 linear array operating at 5 MHz connected to a Verasonics ultrasound imaging system. In the image of FIG. 7B, 55.5 dB of dynamic range is displayed. The image of FIG. 7B is the result of coherent summation over 128 sets of random delay encoding vectors spanning 0 to 1 wavelength. As shown in the image, for example, the contrast in anechoic lesions at 60 mm and 80 mm depth is reduced as compared to the 30 wavelength encoded delays used in FIG. 5B. Therefore, the anechoic target 501 at 80 mm depth in FIG. 5B is not apparent in FIG. 7B.

Figures 8A, 8B:
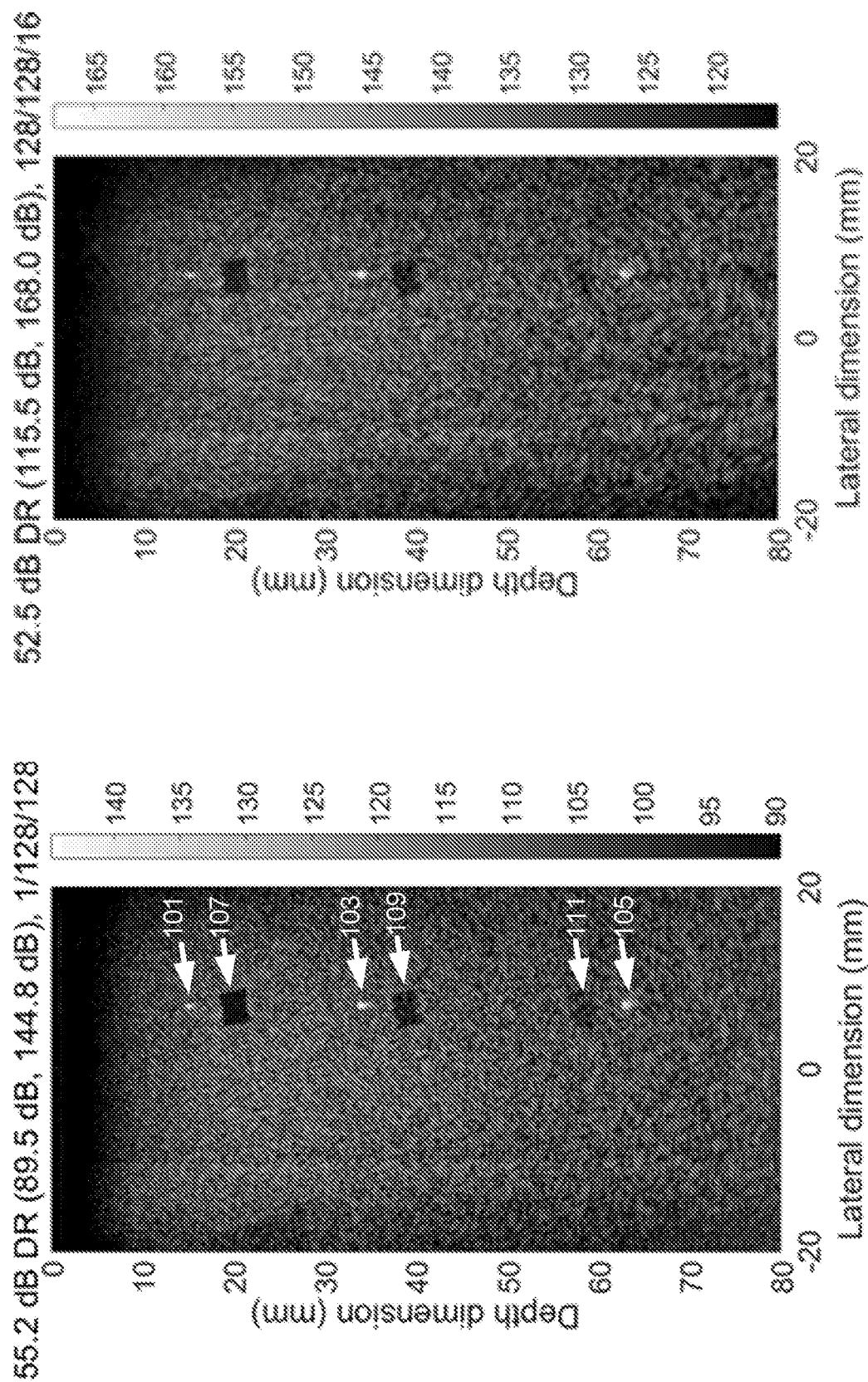
FIGS. 8A and 8B show, respectively, exemplary images obtained through full synthetic transmit aperture and delay encoded synthetic transmit aperture for 16 sets of delays spanning 0 to 1 wavelength.

FIGS. 8A and 8B show, respectively, exemplary images obtained through full synthetic transmit aperture and delay encoded synthetic transmit aperture for 16 sets of delays spanning 0 to 1 wavelength. FIG. 8A shows the full synthetic transmit aperture image (same as FIG. 1) captured with 55.2 dB of dynamic range for comparison. FIG. 8B shows the delay encoded synthetic transmit aperture image of the example CIRS model 044 ultrasound phantom generated using a Philips/ATL L7-5 linear array operating at 5 MHz connected to a Verasonics ultrasound imaging system. In the image of FIG. 8B, 52.5 dB of dynamic range is displayed. The image of FIG. 8B is the result of coherent summation over 16 sets of random delay encoding vectors spanning 0 to 1 wavelength. As shown in the image, for example, there are slight improvements in artifacts around the wires as compared to 30 wavelength encoded delays used in FIG. 6B, but a reduction in contrast in the two deepest lesions at 60 mm and 80 mm. Striping artifacts over depth are due to slight destructive interference from non-optimal delay selection. Also, the noise-free depth-of-penetration is still much improved for the delay encoded image, as compared to FIG. 8A for example, albeit with 8× the frame rate speed.

In some embodiments of the disclosed methods, the transmissions are electrically and acoustically isolated from the receiver, e.g., such that the crosstalk results in no perceptible artifacts in the resulting image. The transmit delays may be arbitrary in both space and time. For example, randomly delayed transmissions may proceed at random pulse-repetition intervals independently on all elements. Moreover, the pulse repetition interval need not equal or exceed the round-trip time from transmission to reception as is typically enforced in ultrasound imaging. Additionally, since transmits may be distributed arbitrarily over space and time, some embodiments also include using only one set of transmitters combined with transmit multiplexers to allow arbitrary high speed selection of a transmit element. The transmitters may be optimized to transmit arbitrary waveforms. In some embodiments, the receivers may be free running, e.g., constantly recording echoes that are continuously directed into beamformer hardware.

In some embodiments of the disclosed methods, where it may not be possible to electrically isolate transmitters and receivers for simultaneous operation, e.g., using the same array for both transmission and reception, circuitry on all or a subset of the receivers blanks or attenuates the transmit crosstalk signal to below a threshold to reduce image artifacts below the threshold of perception. For example, simultaneous with a transmission, one or more receivers are individually switched off using e.g., a PIN switching diode or similar high speed, high bandwidth switch, thus preventing the transmit signal from saturating the receiver electronics.

In some embodiments of the disclosed methods, the ADC outputs of all or a subset of receiver channels may be digitally signaled to zero-out the transmit crosstalk signal that appears coincident with each transmission, with an adjustable delay and duration.

In some embodiments of the disclosed methods, prior to beamforming, transmit crosstalk signals are rejected using signal processing. Moreover, the rejected signals may be recovered using signal processing, e.g., through application of interpolation or any method or algorithm useful for estimating the missing samples based on spatially (e.g., reciprocity) and/or temporally correlated signals (e.g., filtering) spanning one or more transmitter and/or receiver combination across one or more independent transmit realizations.

In some embodiments of the disclosed methods, in the delay-and-sum beamformer, echo samples corresponding to specific transmitter, receiver, and/or delay combinations that result in an overlapping time of arrival to an image point are rejected, omitted, or weighted based on pre-determined patterns either stored in memory or computed within the beamformer. Moreover, the rejected signals may be recovered using signal processing, e.g., through application of interpolation or any method useful for estimating the missing samples based on spatially and/or temporally correlated signals spanning one or more transmitter and/or receiver combination across one or more independent transmit realizations.

Additional spatial encoding is made possible through consideration of both amplitude and/or phase of the transmitted waveforms. Amplitude encoding is accomplished by modulating the amplitude of the transmitted waveform versus element index or spatial element position. Phase encoding is accomplished by modulating the phase of the transmitted waveform versus element index or spatial element position. In some implementations, amplitude encoding and phase encoding can be accomplished in the same process of the method for temporally and spatially encoding acoustic waveforms. For example, a 4-element amplitude encoding sequence, e.g., given by [0.5 1.0 0.0 0.75], as an example, combined with a 4-element binary phase encoding sequence of [1 −1 1 −1] results in a 4-element amplitude and phase encoded sequence of [0.5 −1.0 0.0 −0.75], i.e. resulting from the elementwise product of the amplitude sequence with the phase sequence.

As discussed above, the best possible imaging speed and resolution is achieved when all spatial frequencies are excited simultaneously or nearly simultaneously in order to mitigate effects of motion. Delay encoding is a path to nearly simultaneous excitation, yet it may introduce noise from undesirable overlapping echoes that average out as more statistically independent delayed echo samples are averaged.

The amplitude and phase of the transmitted waveforms may be varied for each transmission in unique ways such that they encode all spatial frequencies simultaneously and such that they may be decoded exactly or in an approximately exact way with significant SNR gain. For example, for a 4-element aperture, the transmission may have spatial amplitude and phase corresponding to the biphase sequence, [1 −1 1 1], which has a corresponding circular autocorrelation of [4 0 0 0], which is exactly a Kronecker delta function with amplitude 4. Likewise, for an 8-element aperture, the biphase amplitude modulated sequence, e.g., given by [1.00000 −0.91546 0.75184 0.99877 0.91478 0.23430 −0.50953 −0.31760] for example, has a circular autocorrelation given by [4.6531 4.3314e-09 −9.2177e-10 6.1084e-09 1.6652e-08 6.1084e-09 −9.2177e-10 4.3314e-09], which is approximately a Kronecker delta function with amplitude 4.6531.

Figure 9A:
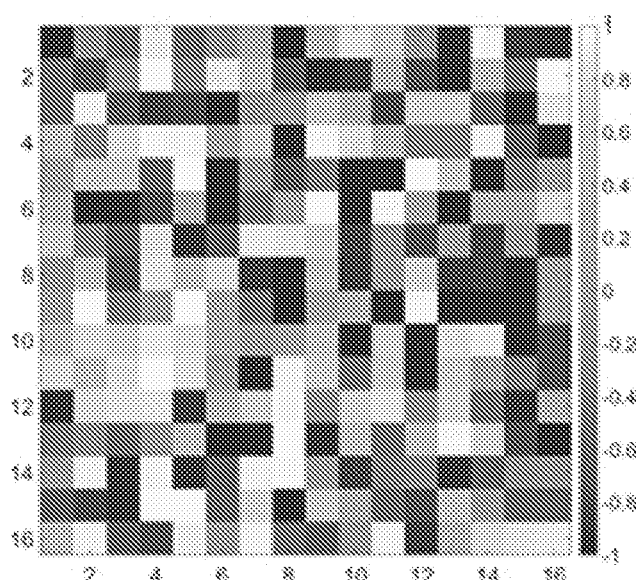
FIG. 9A shows an example of a numerically optimized set of 16, length 16 random amplitude and phase transmit spatial encoding vectors.
Figure 9B:
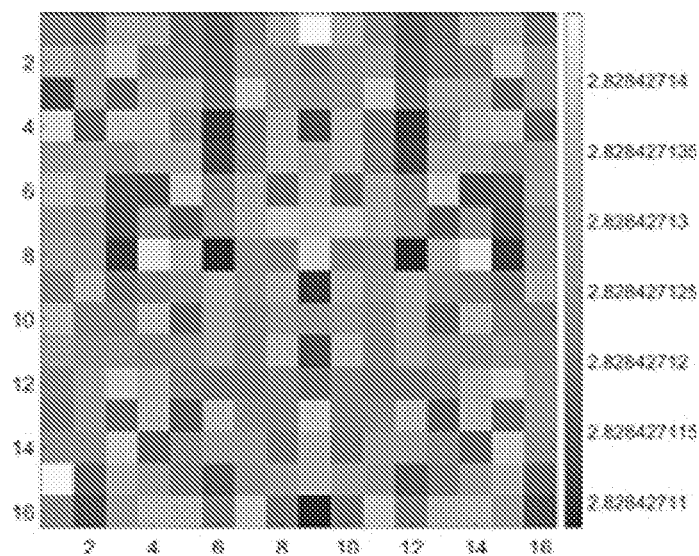
FIG. 9B shows an example of the magnitude of the discrete Fourier transform corresponding to FIG. 9A.
Figure 9C:
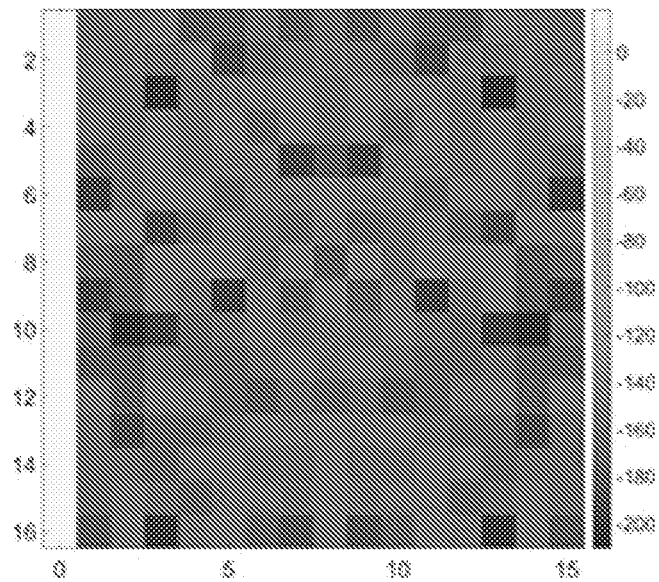
FIG. 9C shows an example of the circular autocorrelation of the spatial encodings corresponding to FIG. 9A.

In some implementations, arbitrary length sequences may be numerically optimized to maximize the lag-zero circular autocorrelation and minimize all other lags. An example of a numerically optimized set of 16, length 16 random amplitude and phase transmit spatial encoding vectors is shown in FIG. 9A, where transmit vectors are in each row. The corresponding magnitude of the discrete Fourier transform is shown in FIG. 9B. DC value is leftmost in each row. Note that the spectra are approximately equal to $\sqrt{8}$ for all spatial frequencies across all encoding vectors. The decoding properties of each transmit vector are assessed by computing the circular autocorrelation of the transmit vector. FIG. 9C shows the circular autocorrelation of the spatial encodings. The scale is shown in dB, where the maximum is approximately equal to 8 for each encoding vector and the side lobes are below −170 dB for all lags greater than 0, thus an excellent approximation to a Kronecker delta function. Each row vector compresses to an extremely good approximation to a Kronecker delta function with an optimized linear gain of 8 for each length 16 vector. Note that this specific example of an encoding matrix requires a transmitter that allows for arbitrary control of amplitude and phase inversion, which is well within the purview of disclosed technology.

In some implementations, the arbitrary length sequences may also be optimized for 2-dimensional matrices to achieve encoded transmission on, for example, 2-D arrays. Moreover, the sequences may be optimized for 3-dimensional matrices to achieve encoded transmission in 2 spatial dimensions plus the time dimension, which may achieve 3-dimensional encoding. The decoding may be applied through direct circular matched filter convolution with the encoding vector/matrix or it may be applied in the frequency domain through the use of the discrete Fourier transform, or equivalently, the fast Fourier transform when computationally preferable.

The arbitrary length sequences also have a close relationship to uniformly redundant arrays (URAs), which are mask patterns primarily applied to optical imaging. The URAs are binary, and they share similar Kronecker delta properties when correlated with their matched pattern. The URAs essentially enable pinhole-like imaging resolution using a much larger aperture, thus, much more received light and higher SNR. The URAs are primarily limited to far field imaging; however, ultrasound imaging is well known to occur in the near field of an aperture.

The disclosed techniques have the unique property of leveraging a far field spatial encoding strategy to address a near field imaging problem that has not been contemplated before in ultrasound imaging. As the delay component of delay-and-sum beamformer transforms near field echoes into their far field equivalents, the spatial decoding is applied to delayed echo samples prior to summation. The disclosed techniques can apply decoding prior to summation at the sample delay step of the delay-and-sum beamformer, i.e. the decoding is applied to echo samples with different delays, which represents a radical departure from traditional spatial encoding/decoding vis a vis Hadamard spatial encoding, where the decoding is applied to echo samples with the same delay.

In some embodiments, the encoding vectors may be complementary. For example, the encoding and decoding vectors may not be identical, however, their circular cross-correlation results in a Kronecker delta function, while their individual circular autocorrelations are not Kronecker delta functions. This may also provide for obfuscation of the observable encoding vector from reverse engineering that provides an alternative to other obfuscating techniques such as vector scrambling, convolution with other random vectors, etc.

Example implementations of the disclosed amplitude and phase and delay encoding strategy was tested in an example simulation for point 9 targets, for a 128 sets of amplitude and phase encoding vectors combined with 128 sets of random delay encoding vectors spanning 0 to 227.5 wavelengths. The simulated array used a Philips L7-4 linear array operating at 5 MHz, and the simulation was performed using the Verasonics imaging system software simulator.

Figure 11:
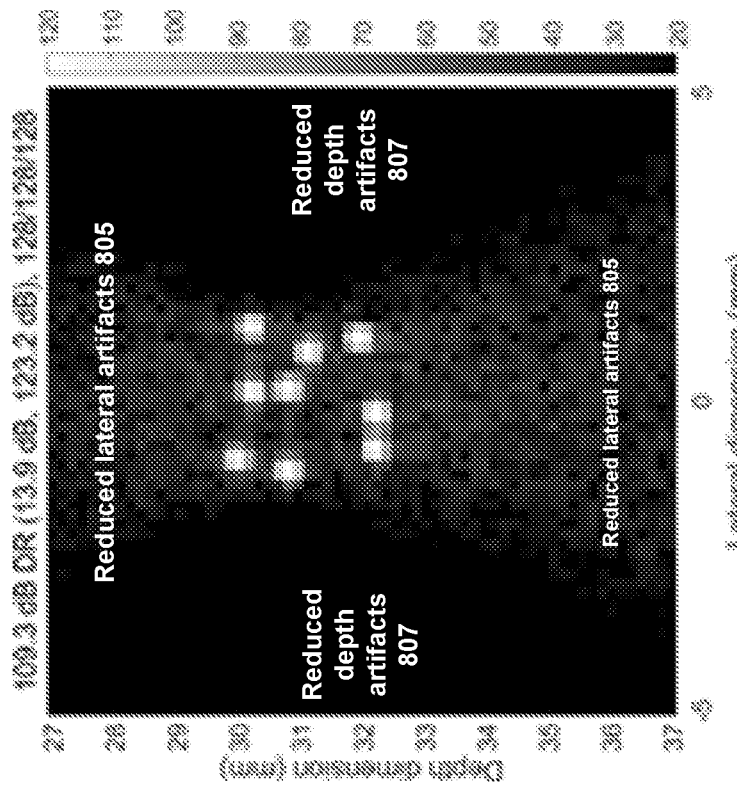
FIGS. 10 and 11 show exemplary images of 9 point targets beamformed with delay encoding only and with delay encoding combined with amplitude and phase encoding.
Figure 10:
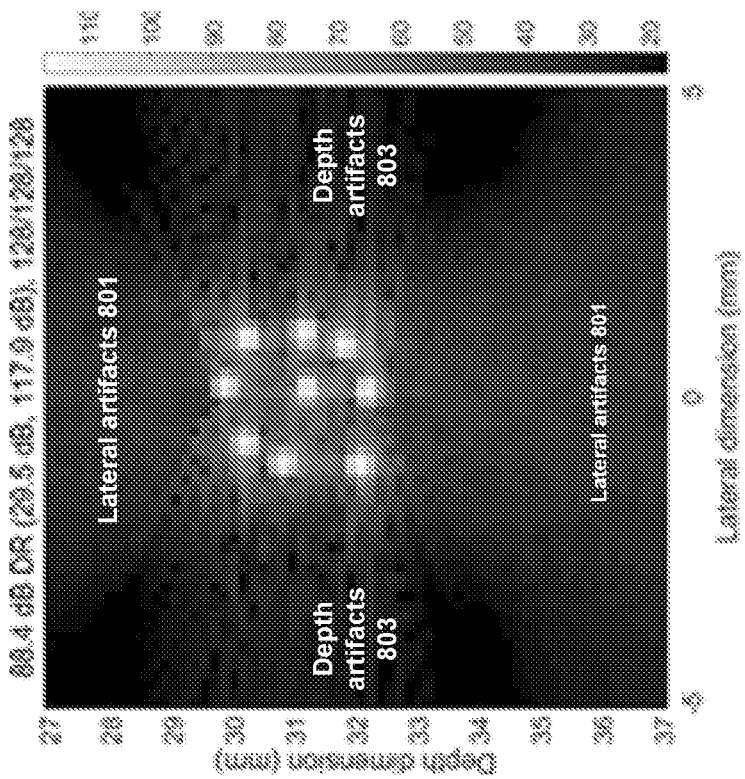

FIGS. 10 and 11 show exemplary images of 9 point targets beamformed with delay encoding only (FIG. 10) and with delay encoding combined with amplitude and phase encoding (FIG. 11). FIG. 10 shows an image of 9 point targets beamformed with delay encoding only, in which 100 dB dynamic range is displayed. Note artifacts (e.g., scattering grey pixels) due to echo overlap in the lateral dimension (labeled 801) and depth dimension (labeled 803). FIG. 11 shows an image of 9 point targets beamformed with delay encoding combined with amplitude and phase encoding, in which 100 dB dynamic range is displayed. As shown in FIG. 11, for example, the artifacts are greatly reduced in the lateral dimension (labeled 805), and there is artifact reduction in the depth dimension (labeled 807), e.g., due to amplitude and phase spatial encoding. Also, it is noted that there is greater absolute image magnitude of 123.2 dB vs. 117.9 dB. In some embodiments, combined encoding can be implemented, as well.

A combination of amplitude, phase, and delay encoding may be utilized to improve the speed of data acquisition and reduce image artifacts in all aforementioned embodiments of spatial delay encoding. For example, for a given field-of-view, the encoding delays may be optimized to minimize the average occurrence of overlapping echoes across the entire image. Additionally, refinements in the interframe and intraframe post-image processing can have a major impact on improving image quality without significant changes to the embodiments as disclosed.

The disclosed methods and systems are fully compatible with coded waveforms, and they will likely benefit from channel isolation and waveform diversity aspects of coded waveform transmission.

Figure 12:
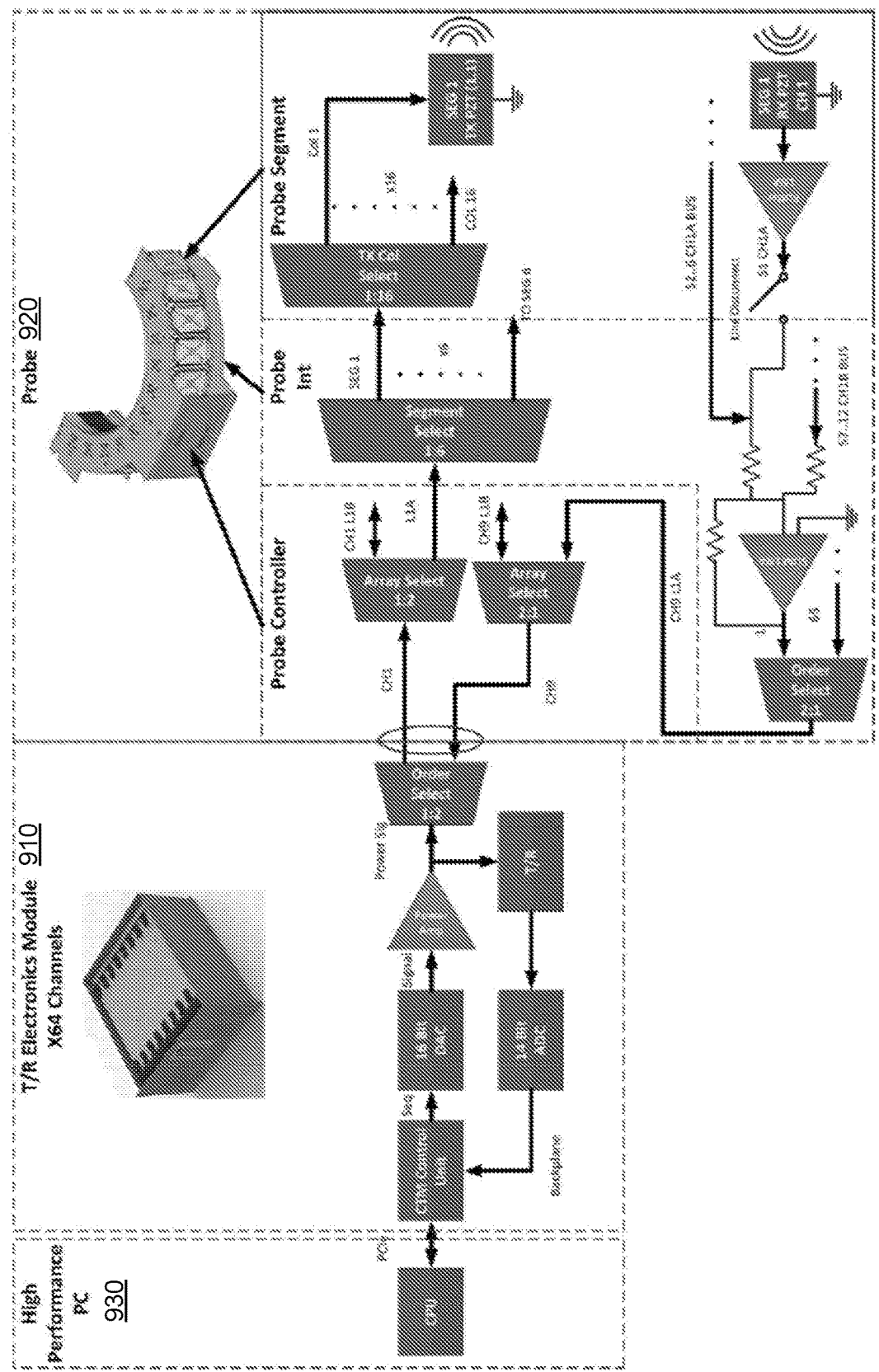
FIG. 12 shows a block diagram of one example embodiment of a synthetic transmit aperture acoustic system of the disclosed technology.

FIG. 12 shows a block diagram of one example synthetic transmit aperture acoustic system that can accommodate the disclosed technology. As shown in FIG. 12, the system includes a transmit/receive electronics module 910 in electrical communication with an acoustic probe device 920 and with a data processing unit or computer 930. The transmit/receive electronics module 910 is configured to generate the individual coded waveforms on multiple channels transferred to the probe device 920 for transmitting and receiving one or more composite waveforms (e.g., coherent, spread-spectrum, instantaneous-wideband, coded waveforms) based on the individual-generated coded waveforms. The probe device 920 includes a probe controller unit in communication with a probe interface unit that is in communication with each probe transducer segments. For transmit, the probe controller is operable to receive the waveform information from the transmit/receive electronics module 910 of the generated discrete waveforms carried on the multiple communication channels, which are transduced by the transducer elements on the probe transducer segments. The probe interface includes circuitry to route the waveform signals to selected transducer elements. The probe device 920 can include one transducer segment or an array of multiple transducer segments arranged on a section of the housing body having a particular geometry that makes contact with a body structure of the subject. In some embodiments, for example, the section can include a flat shape, whereas in other embodiments, the section can include a curved shape.

Figure 13:
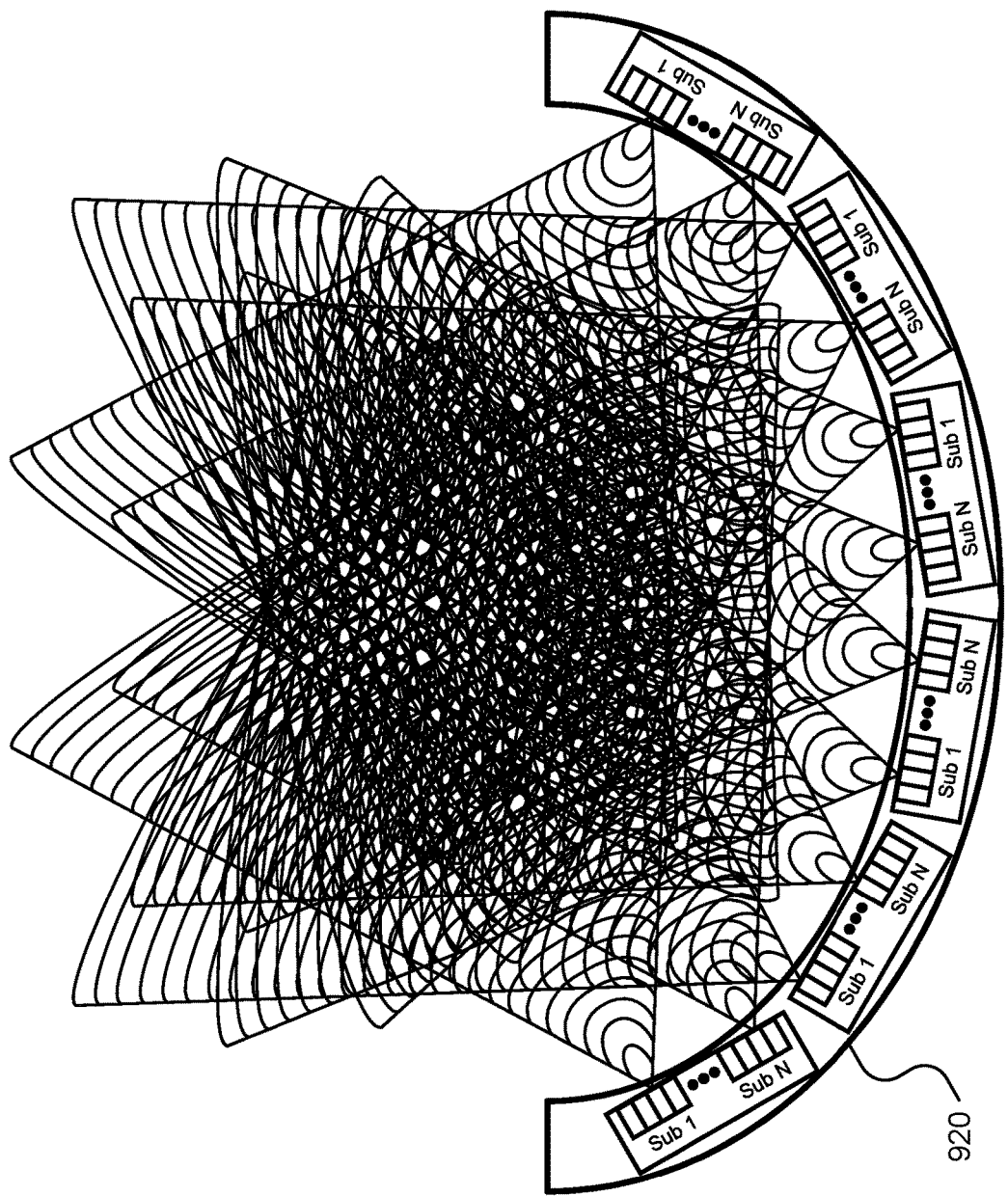
FIG. 13 shows a diagram of exemplary composite ultrasound beams generated by transducer arrays on multiple transducer segments that forms a synthetic transmit aperture beam from multiple transmitting positions along a 180° curvature of the probe.

FIG. 13 shows a diagram of exemplary composite ultrasound beams generated by transducer sub-arrays on multiple transducer segments that forms a synthetic transmit aperture beam from multiple transmitting positions along a 180° curvature of the probe 920. As shown in the diagram, a probe 920 includes multiple transducer segments used to form one or more real aperture sub-arrays Sub 1, Sub 2, . . . Sub N on one or more of the transducer segments. Some or all of the transducer elements that form the transducer array can transmit (e.g., either sequentially, simultaneously or randomly) one or more composite acoustic waveforms of individual, mutually orthogonal, coded acoustic waveforms transmitted to a target from multiple sub-array phase center positions to form a synthetic transmit aperture for ultrasound imaging. In some implementations, different transducer elements on the transducer segments can be selected to form the receive array to receive the returned acoustic waveforms corresponding to the transmitted acoustic waveform (formed based on the individual, mutually orthogonal, coded acoustic waveforms), in which the received acoustic waveforms are scattered back and returned (e.g., reflected, refracted, diffracted, delayed, and/or attenuated) from at least part of the target. Whereas, in some implementations, some or all of the transducer elements that form the transmit array can also receive the returned acoustic waveforms corresponding to the transmitted acoustic waveform. The received individual acoustic waveforms thereby form one or more received composite waveforms that correspond to the transmitted composite acoustic waveforms.

Figure 14:
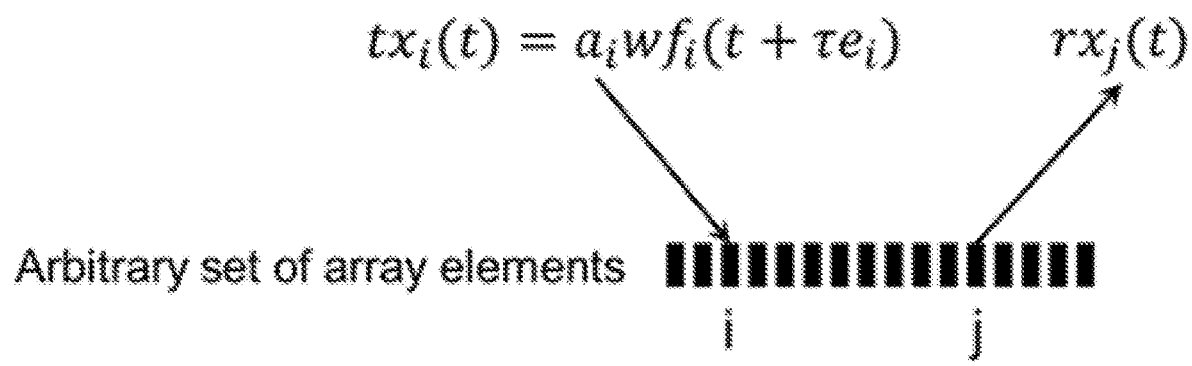
FIG. 14 shows a diagram of an arbitrary set of transducer array elements corresponding to a mathematical description of the spatial and temporal transmit encoded waveforms and the receive waveforms before decoding.

FIG. 14 shows a mathematical expression of encoded transmission on an arbitrary set of array elements. The waveform, $tx_i(t)$, drives $i^{th}$ array element with waveform encoding function, $wf_i(t)$, amplitude and phase encoding vector, $\alpha_i$, and delay encoding vector, $\tau e_i$. The echo waveform $rx_j(t)$ is received from the $j^{th}$ array element. All or a subset of array elements are driven coherently in the same transmission event.

Figure 15:
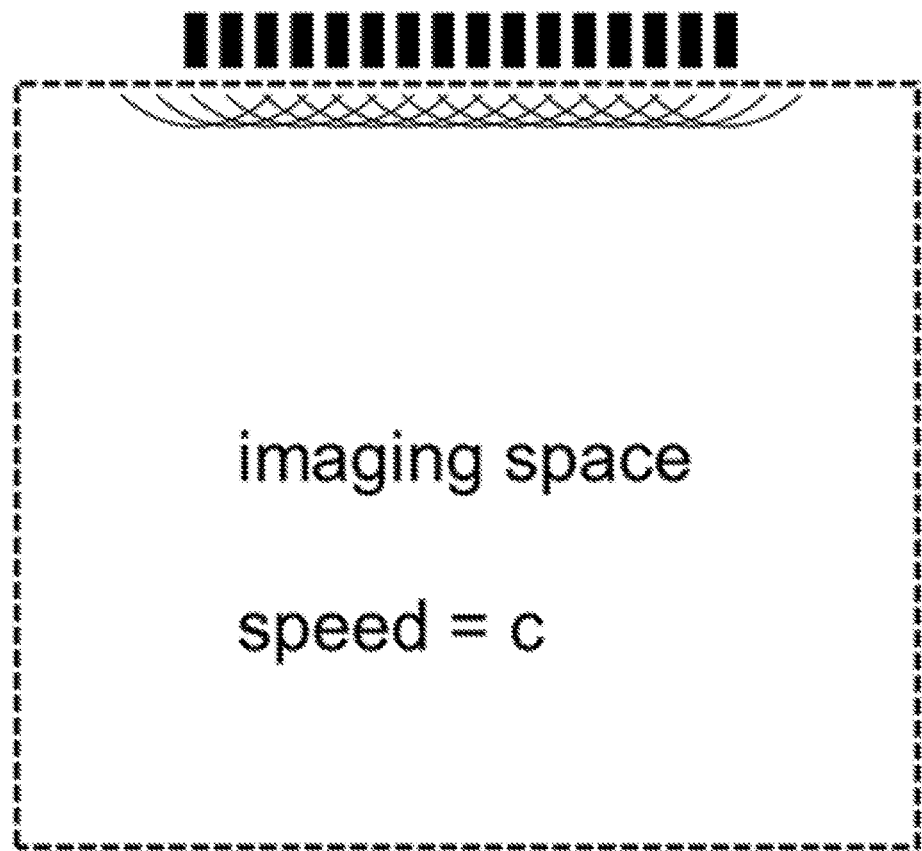
FIG. 15 shows a diagram of a transducer array elements depicting an example of transmission on a 16-element array with constant delay.

FIG. 15 shows an exemplary depiction of coherent transmission from 16 array elements into a medium with propagation speed, c. The depicted wavefronts each emanate from a single element with constant delay across the aperture. The each wavefront may correspond to a unique waveform encoding and/or amplitude and phase encoding.

Figure 16:
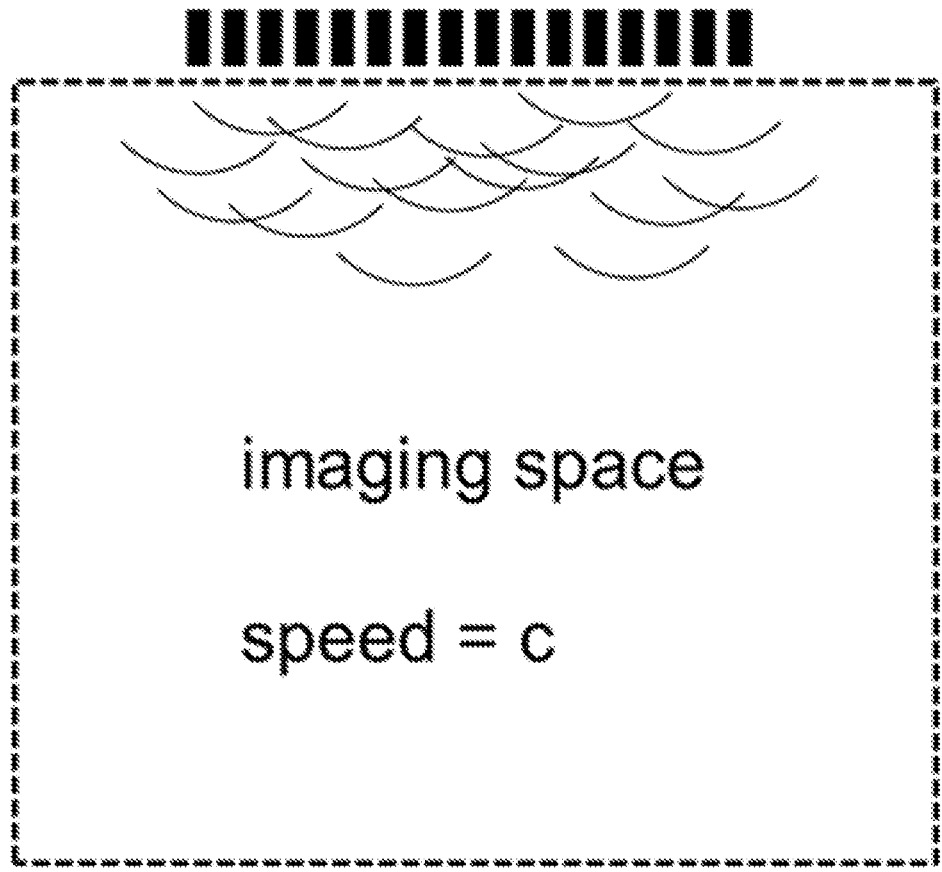
FIG. 16 shows a diagram of a transducer array elements depicting an example of transmission on a 16-element array with random encoded delay.

FIG. 16 shows an exemplary depiction of coherent transmission from 16 array elements into a medium with propagation speed, c. The depicted wavefronts each emanate from a single element with random delay encoding across the aperture. The each wavefront may also correspond to a unique waveform encoding and/or amplitude and phase encoding.

Figure 17:
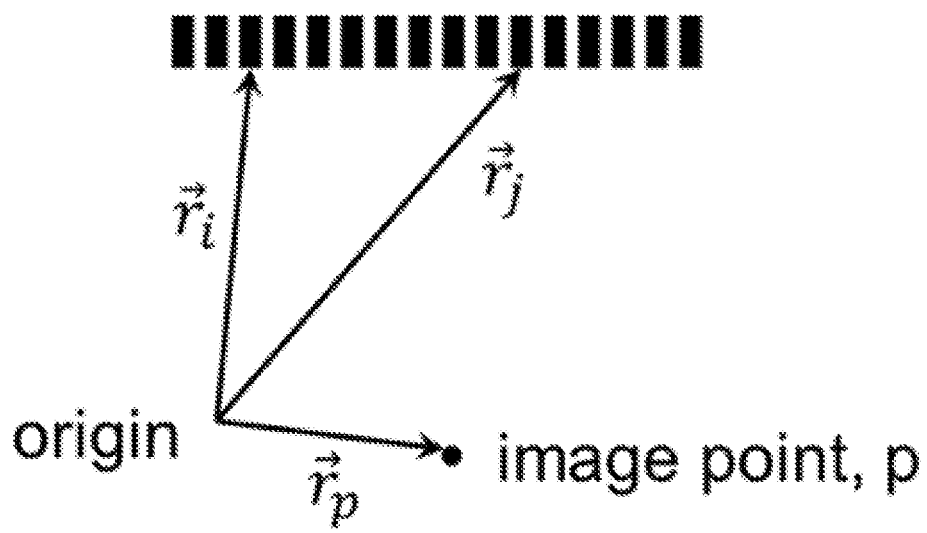
FIG. 17 shows a diagram of an arbitrary set of transducer array elements corresponding to the geometry for encoding, decoding, and beamformation for a single target point p.

FIG. 17 shows the beamforming geometry for an arbitrary set of array elements. The vectors $\vec{r}_i$, $\vec{r}_j$, $\vec{r}_p$ are the 3D vector positions of the transmit element, receive element, and image point, p, respectively, relative to an origin.

In the beamformer, geometric focusing delays are computed according to the roundtrip distance from the $i^{th}$ transmission element to the image point and back to the $j^{th}$ reception element divided by the medium speed, c, as follows:

$$\tau_p(i, j) = \frac{|\vec{r}_p - \vec{r}_i| + |\vec{r}_p - \vec{r}_j|}{c} \qquad \text{Eq. (2)}$$

where the | | operator denotes Euclidean distance of the enclosed vector and $\tau_p(i, j)$ is the focusing delay for point p corresponding to transmit element i and receive element j. Equation (2) is a summary of the delay calculation in a delay-and-sum beamformer.

Figure 18:
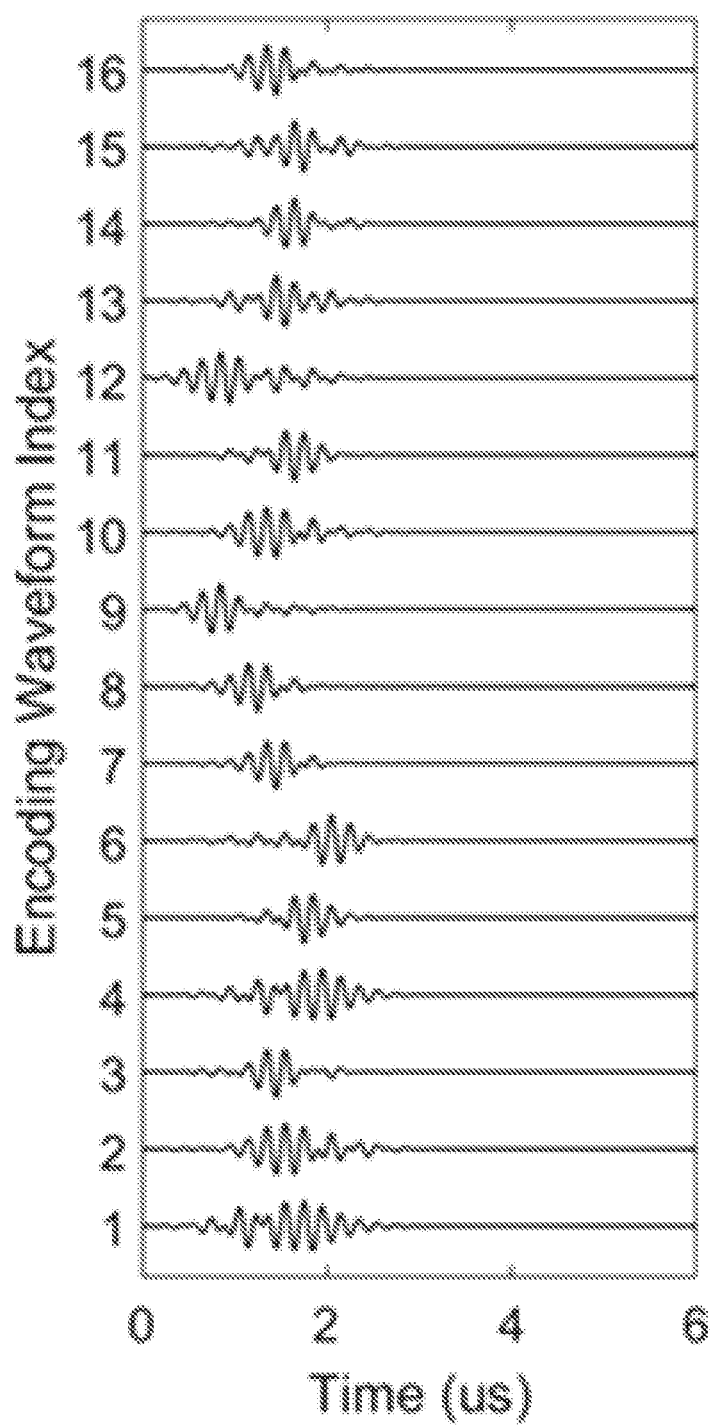
FIG. 18 shows a diagram illustrating 16 different waveforms used for waveform encoding.

FIG. 18 shows exemplary set of 16 independent encoding waveforms each with a center frequency of 5 MHz and a −6 dB fractional bandwidth of 70% and each having nearly ideal linear autocorrelation properties, for example, range lobes below −60 dB.

Figure 19:
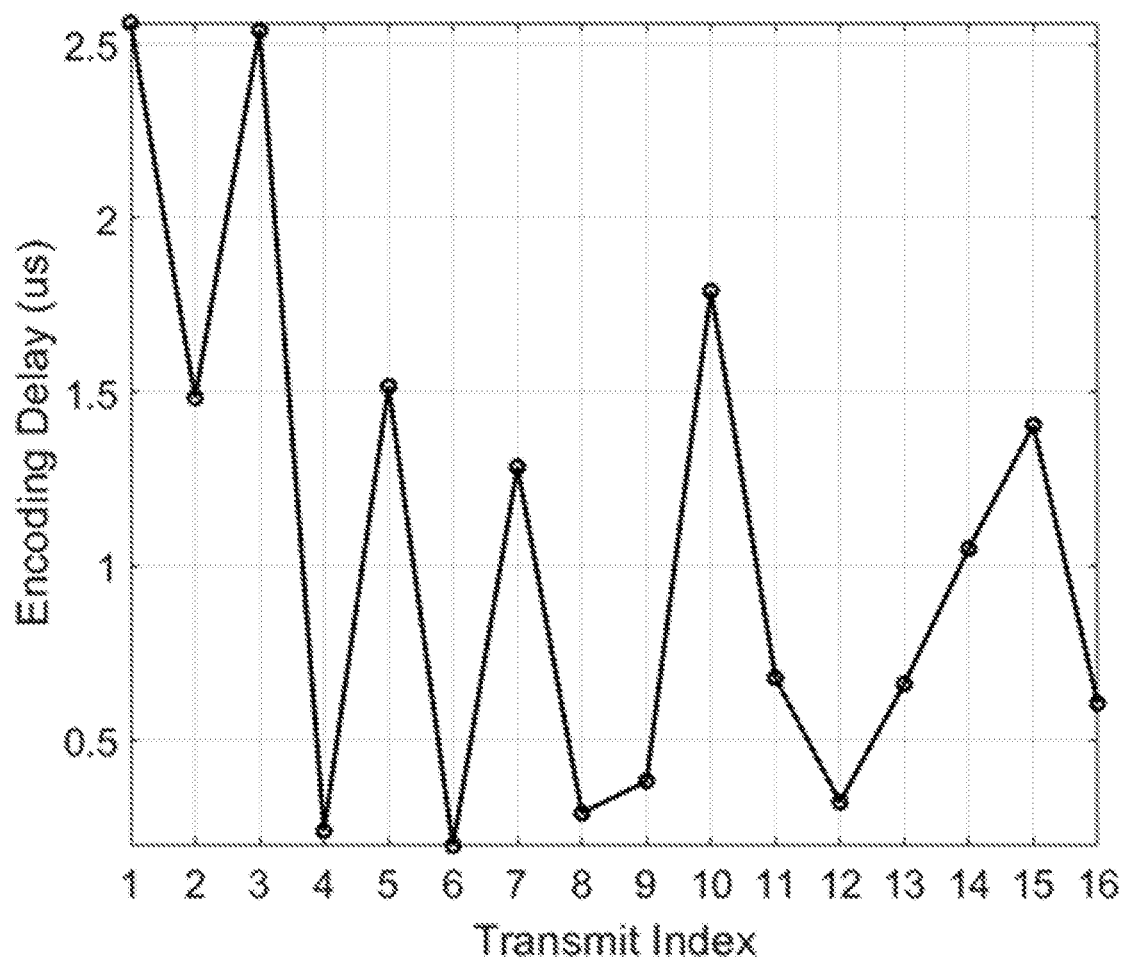
FIG. 19 shows a plot illustrating 16 random delays for delay encoding.

FIG. 19 shows an exemplary sequence of uniformly randomly distributed encoding delays ranging from 0.196 microseconds to 2.56 microseconds.

Figure 20:
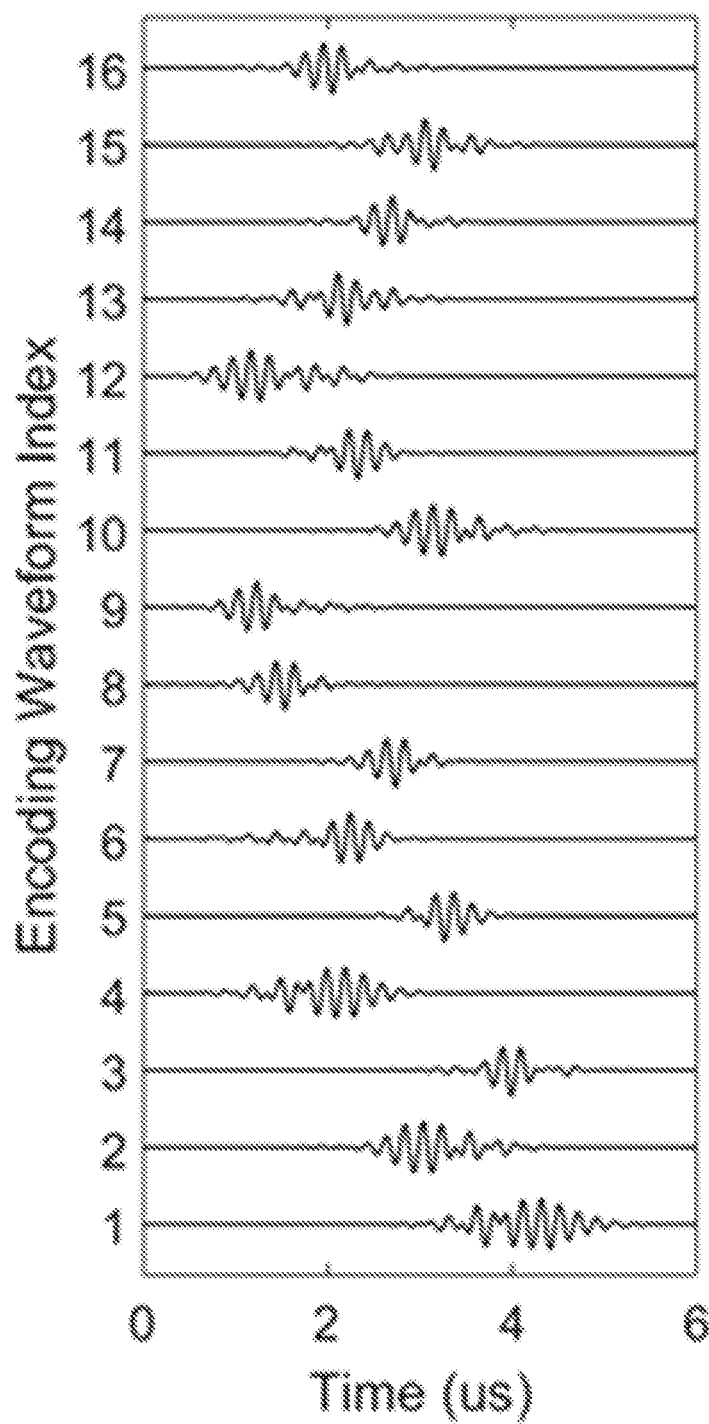
FIG. 20 shows a diagram illustrating 16 different waveforms with delay encoding corresponding to FIG. 19.

FIG. 20 shows the exemplary set of 16 encoding waveforms shown in FIG. 18 with delay encoding as shown in FIG. 19.

Figure 21:
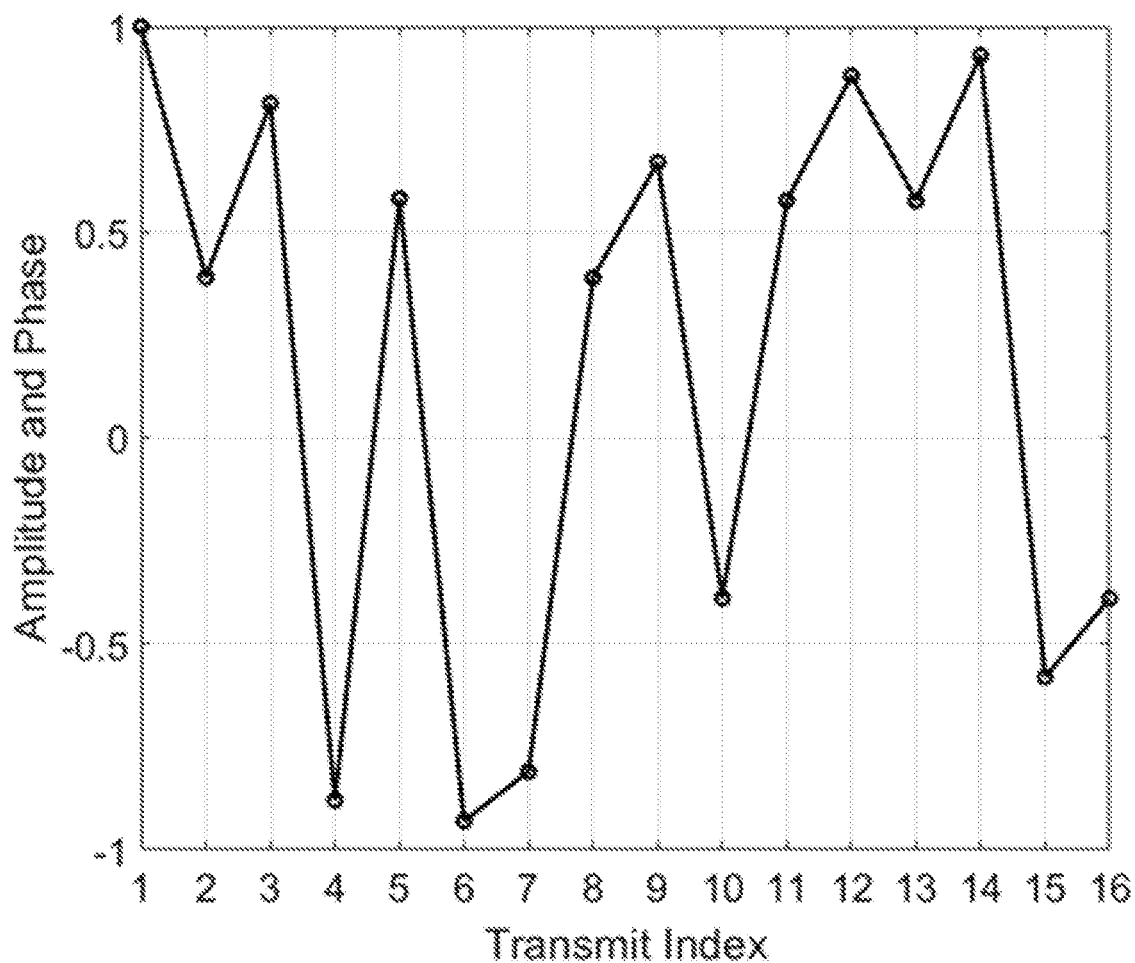
FIG. 21 shows a plot illustrating an example sequence of 16 amplitude and phase values for amplitude and phase encoding.

FIG. 21 shows an exemplary sequence of 16 amplitude and phase encoding values with nearly ideal circular autocorrelation properties.

Figure 22:
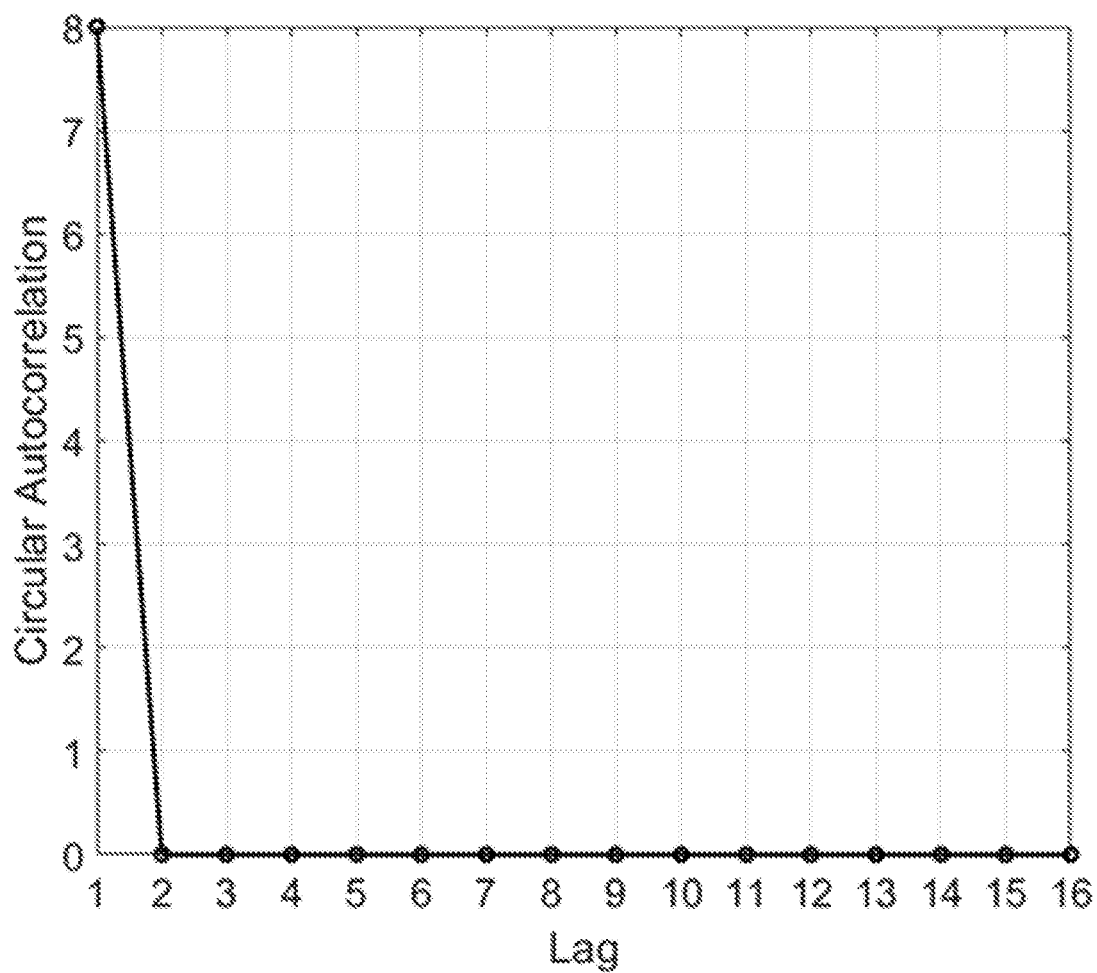
FIG. 22 shows a plot illustrating the circular autocorrelation of the sequence in FIG. 21.

FIG. 22 shows the circular autocorrelation of the sequence shown in FIG. 20, illustrating the nearly ideal Kronecker delta properties of the sequence with non-zero lag values less than 2.09e-08 and a linear gain of 8 at lag zero.

Figure 23:
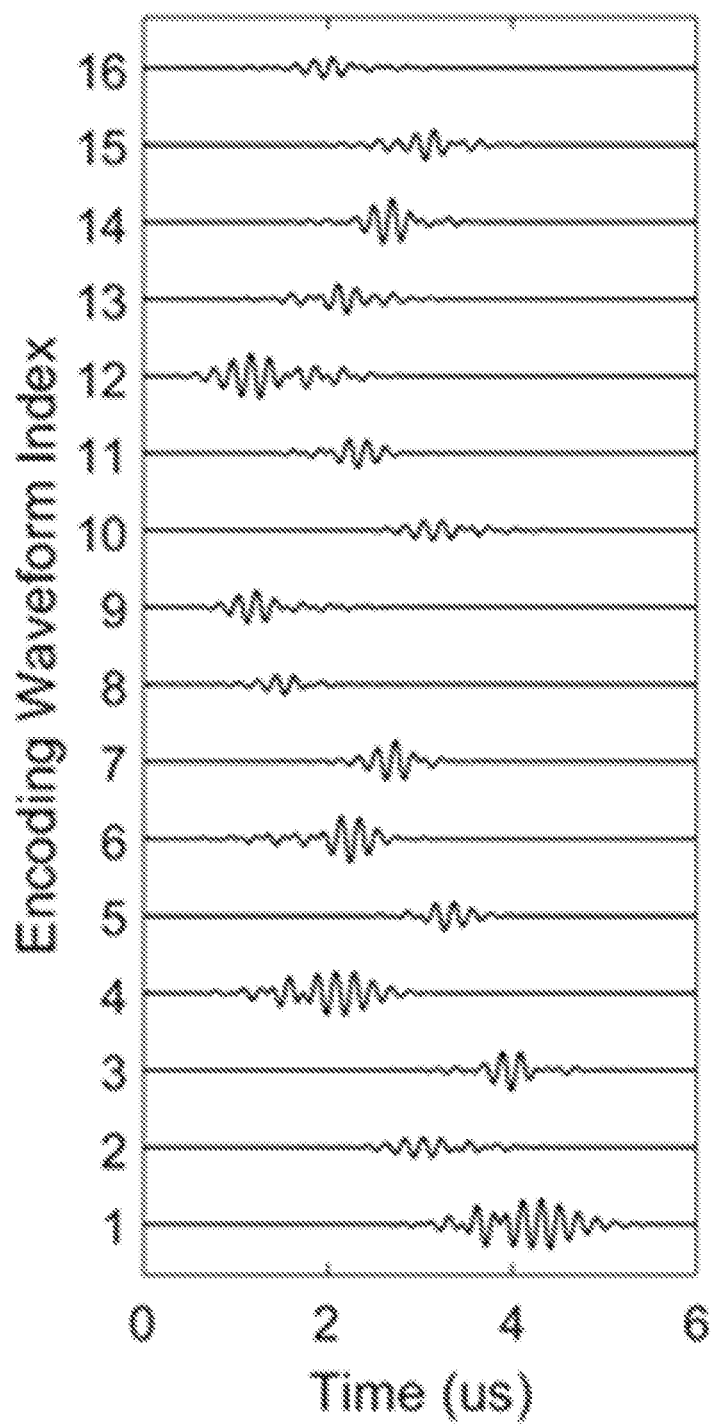
FIG. 23 shows a diagram illustrating 16 different waveforms with delay encoding corresponding to FIG. 19 and amplitude and phase encoding corresponding to FIG. 21.

FIG. 23 shows the exemplary set of 16 encoding waveforms shown in FIG. 20 with amplitude and phase encoding as shown in FIG. 21.

Figure 24:
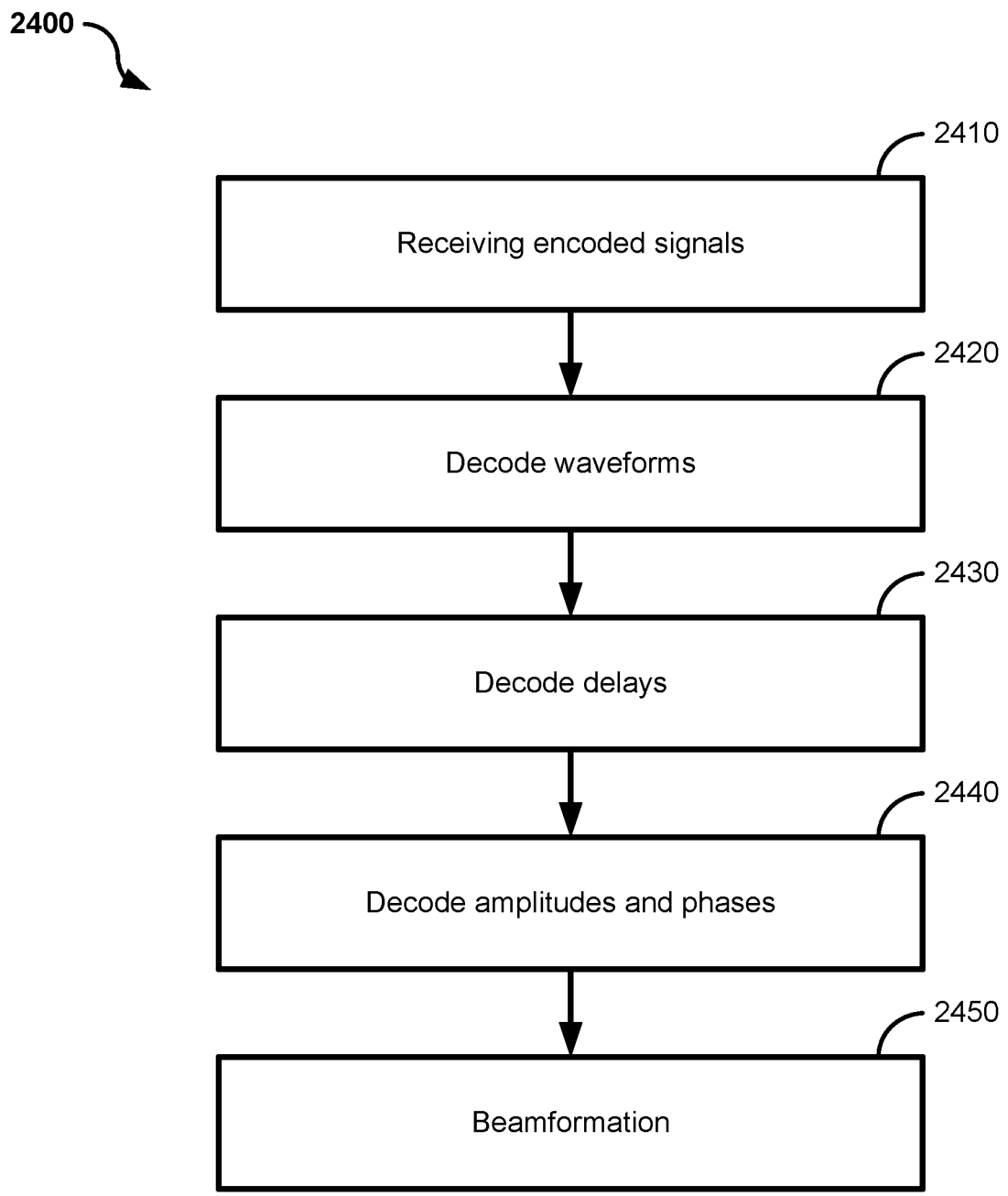
FIG. 24 shows a diagram of an example embodiment for a decoding method in accordance with the present technology.

FIG. 24 shows a diagram of an example embodiment for a decoding method 2400 in accordance with the present technology. In some implementations, for example, the method 2400 can be implemented at the process 240 of the method 200. In various implementations of the method 2400, e.g., depending on which encoding strategies are utilized, the exemplary decoding method 2400 can include up to three stages comprised of (i) coded waveform decoding (e.g., decoding the unique set of encoded waveforms, which can include arbitrary waveforms that simultaneously satisfy properties of range compression and orthogonality, and/or frequency-coded and/or phase-coded waveforms), (ii) transmit delay pattern decoding, and (iii) transmit amplitude and phase pattern decoding, in which the coded waveform decoding stage, the transmit delay pattern decoding stage, and/or the transmit amplitude and phase pattern decoding stage is selected based on which of the respective encoding techniques is employed, e.g., at the process 210 of the method 200.

After receiving encoded acoustic signals, at 2410 in the diagram of FIG. 24, the decoding method 2400 can include a first decoding phase, which in this example implements a process 2420 to decode coded waveforms. The decoding method 2400 can include a second decoding phase, which in this example implements a process 2430 to decode transmit delays. The decoding method 2400 can include a third decoding phase, which in this example implements a process 2440 to decode amplitudes and phases. The decoding method 2400 can include a beamforming process 2450. The processes of the example decoding method are described below.

The example procedure shown in FIG. 24 presents one order of the decoding stages of the method 2400, including decoding encoded waveforms, decoding transmit delays, and decoding amplitude and phase; however, the procedure is not limited to a specific order of decoding or a specific method of decoding or a specific decoding algorithm.

In the exemplary decoding method 2400 shown in FIG. 24, the first stage includes waveform decoding, in which the $j^{th}$ received echo is filtered with a time-reversed and conjugated version of the $i^{th}$ transmitted waveform, resulting in a partially decoded set of waveforms as follows:

$$rx_{ij}^{(d1)}(t) = rx_{ij}(t) * wf_i^*(-t) \quad \text{Eq. (3)}$$

where the * operator denotes convolution, the * operator denotes conjugation, and the superscript (d1) denotes the first decoding. Note that the waveform received on element j due to transmission on element i is given by $rx_{ij}^{(d1)}(t)$, e.g. there is now a form of separation between the echo components in the $j^{th}$ received echo corresponding to the $i^{th}$ transmission. Here, $r_{ij}^{(d1)}$ is a 2D beamformer sample matrix where the $i^{th}$ row is referenced according to transmit index i and the $j^{th}$ column is referenced according to receive index j.

The second stage of the decoding method 2400 can include a delay decoding process. The output of the waveform decoding stage is delayed for an image point p using geometry shown in FIG. 17 according to the delay calculation in Equation (2) in addition to the encoding delay $\tau e_i$ shown in FIG. 14 according to the following:

$$rx_{ij}^{(d2)} = rx_{ij}^{(d1)}(\tau_p(i,j) + \tau e_i) \quad \text{Eq. (4)}$$

where the superscript (d2) denotes the second decoding. Here, $rx_{ij}^{(d2)}$ is a 2D beamformer sample matrix where the $i^{th}$ row is referenced according to transmit index i and the $j^{th}$ column is referenced according to receive index j.

The third stage of the decoding method 2400 can include amplitude and phase decoding. The output of the delay decoding stage is decoded with a function $f_\alpha(X)$, which is a function of the the amplitude and phase encoding vector $\alpha_i$, resulting in a three-times decoded set of echo as follows:

$$rx_{ij}^{(d3)} = f_\alpha(rx_{ij}^{(d2)}) \quad \text{Eq. (5)}$$

where in one possible embodiment, $f_\alpha(X)$ is the circular correlation between the column vector $\alpha_i$ and each column of X, where X is a 2D matrix. Here, $rx_{ij}^{(d3)}$ is a 2D beamformer sample matrix where the $i^{th}$ row is referenced according to transmit index i and the $j^{th}$ column is referenced according to receive index j.

In the exemplary embodiment, the beamformed sample for point p is obtained by a weighted summation over all decoded transmitter and receiver combinations as follows:

$$b_p = \sum_i \sum_j w_p(i,j) rx_{ij}^{(d3)} \quad \text{Eq. (6)}$$

where the weighting or apodization function $w_p(i,j)$ is a function of the image point p, transmission element i, and reception element j. The beamformed sample $b_p$, may be obtained by combining the decoded echo samples other ways, for example, using a nonlinear and/or adaptive beamformer.

In the exemplary embodiment, the beamformed sample $b_p$ may be obtained for multiple independent transmissions where each transmission utilizes an independent set of encoding waveforms, encoding amplitude and phase, and/or encoding delays. Denoting the index of the transmission event as k, and the beamformed sample for each transmission as $b_p^k$, the beamformed sample from multiple transmissions may be found by summing over multiple transmissions as follows:

$$\hat{b}_p = \sum_k b_p^k \quad \text{Eq. (7)}$$

where $\hat{b}_p$ denotes an estimated version of $b_p$.

Likewise, the beamformed sample sequence $b_p^k$ may also be filtered using a finite impulse response (FIR) and/or infinite impulse response filter (IIR) and/or a nonlinear filter such as a windowed median filter and/or a statistically optimal filter such as a Kalman filter.

Although the aforementioned encoding and decoding scheme was implicitly described for a 1D array, it may be extended to any geometry by simply applying the appropriate array element indexing scheme.

In some example implementations, an optimization may be performed to fine tune the entire encoding and decoding process. For example, encoding waveforms, encoding amplitudes, and/or encoding delays may be numerically varied by an optimizer to minimize the value of an objection function. The objective function would seek to minimize image artifacts in the encoded synthetic transmission aperture image given by $I_{ESTA}$ relative to an ideally beamformed image based on full synthetic transmission aperture given by $I_{FSTA}$. For example, a nonlinear optimization defined as follows:

$$\operatorname*{argmin}_{\substack{\alpha_i \\ wf_i(t) \\ \tau e_i}} \sum |I_{FSTA} - I_{ESTA}(\alpha_i, wf_i(t), \tau e_i)|^2 \quad \text{Eq. (8)}$$

where the summation is taken over the magnitude squared of all image samples. The nonlinear optimizer solves for the best encoding parameters given a fixed decoding procedure, for example, according to the previously described decoding procedure.

The example optimization may also be performed over unique sets of $\alpha_i$, $wf_i(t)$, and $\tau e_i$ and corresponding images $I_{ESTA}$.

The example optimization may be accomplished using nonlinear machine learning algorithms. For example, a set of encoding parameters is learned using a machine learning algorithm such that the error between the training image set based on full synthetic aperture and the encoded synthetic aperture image set is minimized.

The example optimization may be accomplished online using an imaging system within the optimization or machine learning loop to generate both the training image set and the output image set.

The example optimization may be accomplished offline using a full synthetic aperture data set with artificially imposed waveform encoding, amplitude and phase encoding, and delay encoding.

EXAMPLES

In some embodiments in accordance with the present technology (example A1), a probe device to interface a body structure of a biological subject includes one or more transducer segments comprising an array of transducer elements, and a probe controller in communication with the array of transducer elements to select a first subset of transducer elements of the array to transmit waveforms, and to select a second subset of transducer elements of the array to receive returned waveforms, in which the first subset of transducer elements are arranged to transmit the waveforms toward a target volume in the biological subject and the second subset of transducer elements are arranged to receive the returned waveforms that return from at least part of the target volume, and the waveforms are transmitted in accordance with a predetermined transmit delay pattern. The probe device is operable to transmit, at the target volume, spatially and temporally encoded waveforms that include a predetermined (i) unique set of waveforms, (ii) transmit delay pattern, and/or (iii) transmit amplitude and phase pattern; such that, after receiving returned acoustic waveforms from the target, the returned waveforms are decoded by processing waveform components corresponding to each transmit transducer element are separated from the waveforms on each receive transducer element resulting in a set of waveforms representative of a full synthetic transmit aperture acquisition.

Example A2 includes the probe device of example A1, wherein the predetermined transmit delay pattern comprises a set of random time delays.

Example A3 includes the probe device of example A2, wherein the set of random time delays is a uniform distribution of random values within a range spanning from zero to a maximum tolerated standoff distance of the array of transducer elements.

Example A4 includes the probe device of example A1, wherein the first subset of transducer elements is different from the second subset of transducer elements.

Example A5 includes the probe device of example A1, wherein the first subset of transducer elements is the same as the second subset of transducer elements.

Example A6 includes the probe device of example A5, wherein the second subset of transducer elements attenuates a transmit crosstalk signal to reduce image artifacts.

Example A7 includes the probe device of example A1, wherein the waveforms have different amplitudes for each transmission.

Example A8 includes the probe device of example A1, wherein waveforms have different phases for each transmission.

Example A9 includes the probe device of example A1, wherein different waveforms are used for each transmission.

In some embodiments in accordance with the present technology (example A10), a method of signal transmission includes transmitting by a first transducer element, after a time delay associated with the first transducer element, waveforms towards a target volume in a biological subject; receiving by a second transducer element, after a round-trip time between the first transducer element and the second transducer element, returned waveforms that return from at least part of the target volume; identifying the first transducer element that contributes to the returned acoustic waveforms based on the time delay and the round-trip time; and processing the returned waveforms based on the identification of the first transducer element to generate an image of the target volume in the biological subject.

Example A11 includes the method of example A10, wherein the time delay is selected from a set of random time delays.

Example A12 includes the method of example A11, wherein the set of random time delays is a uniform distribution of random values within a range spanning from zero to a maximum tolerated standoff distance of the first and second transducer elements.

Example A13 includes the method of example A10, wherein the first transducer element is different from the second transducer element.

Example A14 includes the method of example A10, wherein the first transducer element is the same as the second transducer element.

Example A15 includes the method of example A14, wherein the second transducer element attenuates a transmit crosstalk signal to reduce image artifacts.

Example A16 includes the method of example A10, wherein the waveforms have different amplitudes for each transmission.

Example A17 includes the method of example A10, wherein waveforms have different phases for each transmission.

Example A18 includes the method of example A10, wherein different waveforms are used for each transmission.

In some embodiments in accordance with the present technology (example B1), a method for spatial and temporal encoding of acoustic waveforms in synthetic aperture acoustic imaging includes generating a set of spatially and temporally encoded acoustic waveforms for transmission toward a target volume that includes generating one or more of (i) a unique set of coded waveforms, (ii) a transmit delay pattern of time delays for acoustic waveforms to be transmitted at the target volume, or (iii) a transmit amplitude and phase pattern of the acoustic waveforms to be transmitted at the target volume; coherently transmitting the spatially and temporally encoded acoustic waveforms, toward the target volume, using a spatially-sampled aperture formed on an array of transducer elements for one or more transducer segments of an acoustic probe device, wherein each transducer element used in the transmitting is assigned a first index number 1 to i, wherein i is a number equal to or less than a total number of transducer elements; receiving returned encoded acoustic waveforms on the spatially-sampled aperture, wherein the wherein the transducer elements are assigned a second index number 1 to j, wherein j is a number equal to or less than a total number of transducer elements; decoding the returned encoded acoustic waveforms to isolate the $i^{th}$ transmission on the $j^{th}$ reception that correspond to a set of image points of the target volume; and processing the decoded returned encoded acoustic waveforms to beamform isolated echo samples for each image point of the set of image points of the target volume.

Example B2 includes the method of example B1, further comprising forming image of the target volume by processing data associated with the beamformed isolated echo samples.

Example B3 includes the method of example B1, wherein each time delay in the transmit delay pattern for the acoustic waveforms to be transmitted is selected from a set of random time delays.

Example B4 includes the method of example B3, wherein the set of random time delays includes a uniform distribution of random values within a range spanning from zero to a maximum tolerated standoff distance between two or more transducer elements.

Example B5 includes the method of example B1, wherein the generating the transmit delay pattern of time delays for acoustic waveforms includes generating randomly delayed transmission times to allow transmission of the acoustic waveforms at random pulse-repetition intervals independently on all transducer elements of the array for one or more transducer segments.

Example B6 includes the method of example B1, wherein the generating the transmit amplitude and phase pattern of the acoustic waveforms includes modulating an amplitude and modulating a phase for each acoustic waveform to be transmitted with respect to a transducer element index or a spatial position of the transducer element.

Example B7 includes the method of example B1, wherein the encoded acoustic waveforms have different amplitudes for each transmission.

Example B8 includes the method of example B1 wherein encoded acoustic waveforms have different phases for each transmission.

Example B9 includes the method of example B1, wherein the unique set of coded waveforms include arbitrary waveforms that simultaneously satisfy properties of range compression and orthogonality.

In some embodiments in accordance with the present technology (example B10), an acoustic probe device to interface a body structure of a biological subject includes one or more transducer segments comprising an array of transducer elements; and a probe controller in communication with the array of transducer elements to select a first subset of transducer elements of the array to transmit acoustic waveforms, and to select a second subset of transducer elements of the array to receive returned acoustic waveforms, wherein the first subset of transducer elements are arranged to transmit the acoustic waveforms toward a target volume in the biological subject and the second subset of transducer elements are arranged to receive the returned acoustic waveforms that return from at least part of the target volume, wherein the probe device is operable to transmit the acoustic waveforms in accordance with a predetermined transmit delay pattern that spatially and temporally encodes transmit waveforms such that each of the returned acoustic waveforms is distinguishable from another.

Example B11 includes the device of example B10, wherein the predetermined transmit delay pattern comprises a set of random time delays.

Example B12 includes the device of example B11, wherein the set of random time delays includes a uniform distribution of random values within a range spanning from zero to a maximum tolerated standoff distance of the array of transducer elements.

Example B13 includes the device of example B10, wherein the first subset of transducer elements is different from the second subset of transducer elements.

Example B14 includes the device of example B10, wherein the first subset of transducer elements is the same as the second subset of transducer elements.

Example B15 includes the device of example B14, wherein the second subset of transducer elements attenuates a transmit crosstalk signal to reduce image artifacts.

Example B16 includes the device of example B10, wherein the acoustic waveforms have different amplitudes for each transmission.

Example B17 includes the device of example B10, wherein acoustic waveforms have different phases for each transmission.

Example B18 includes the device of example B10, wherein different frequency-coded or phase-coded waveforms are used for each transmission.

In some embodiments in accordance with the present technology (example B19), a method of signal transmission includes transmitting by a first transducer element, after a time delay associated with the first transducer element, acoustic waveforms towards a target volume in a biological subject; receiving by a second transducer element, after a round-trip time between the first transducer element and the second transducer element, returned acoustic waveforms that return from at least part of the target volume; identifying the first transducer element that contributes to the returned acoustic waveforms based on the time delay and the round-trip time; and processing the returned acoustic waveforms based on the identification of the first transducer element to generate an image of the target volume in the biological subject.

Example B20 includes the method of example B19, wherein the time delay is selected from a set of random time delays.

Example B21 includes the method of example B20, wherein the set of random time delays includes a uniform distribution of random values within a range spanning from zero to a maximum tolerated standoff distance of the first and second transducer elements.

Example B22 includes the method of example B19, wherein the first transducer element is different from the second transducer element.

Example B23 includes the method of example B19, wherein the first transducer element is the same as the second transducer element.

Example B24 includes the method of example B23, wherein the second transducer element attenuates a transmit crosstalk signal to reduce image artifacts.

Example B25 includes the method of example B19, wherein the acoustic waveforms have different amplitudes for each transmission.

Example B26 includes the method of example B19, wherein acoustic waveforms have different phases for each transmission.

Example B27 includes the method of example B19, wherein different frequency-coded or phase-coded waveforms are used for each transmission.

In this description, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for spatial and temporal encoding of acoustic waveforms in synthetic aperture acoustic imaging, comprising:
   generating a set of spatially and temporally encoded acoustic waveforms for transmission toward a target volume that includes generating one or more of (i) a unique set of coded waveforms, (ii) a transmit delay pattern of time delays for acoustic waveforms to be transmitted at the target volume, or (iii) a transmit amplitude and phase pattern of the acoustic waveforms to be transmitted at the target volume;
   coherently transmitting the spatially and temporally encoded acoustic waveforms, toward the target volume, using a spatially-sampled aperture formed on an array of transducer elements for one or more transducer segments of an acoustic probe device, wherein each transducer element used in the transmitting is assigned a first index number 1 to i, wherein i is a number equal to or less than a total number of transducer elements;
   receiving returned encoded acoustic waveforms on the spatially-sampled aperture, wherein the transducer elements are assigned a second index number 1 to j, wherein j is a number equal to or less than the total number of transducer elements;
   decoding the returned encoded acoustic waveforms to isolate the $i^{th}$ transmission on the $j^{th}$ reception that correspond to a set of image points scattered from the target volume; and
   processing the decoded returned encoded acoustic waveforms to beamform isolated echo samples for each image point of the set of image points of the target volume,
   wherein generating the transmit delay pattern of time delays for acoustic waveforms includes generating randomly delayed transmission times to allow transmission of acoustic waveforms at random pulse-repetition intervals independently on all transducer elements of the array for one or more transducer segments.

2. The method of claim 1, further comprising forming image of the target volume by processing data associated with the beamformed isolated echo samples.

3. The method of claim 1, wherein each time delay in the transmit delay pattern for the acoustic waveforms to be transmitted is selected from a set of random time delays; and wherein the set of random time delays corresponds to a uniform distribution of random values within a range spanning from zero to a maximum tolerated standoff distance between two or more transducer elements.

4. The method of claim 1, wherein generating the transmit amplitude and phase pattern of the acoustic waveforms includes modulating an amplitude and modulating a phase for each acoustic waveform to be transmitted with respect to a transducer element index or a spatial position of the transducer element.

5. The method of claim 1, wherein the encoded acoustic waveforms have different amplitudes for each transmission.

6. The method of claim 1, wherein encoded acoustic waveforms have different phases for each transmission.

7. The method of claim 1, wherein the unique set of coded waveforms includes arbitrary waveforms that simultaneously satisfy properties of range compression and orthogonality.

8. An acoustic probe to interface a body structure of a biological subject, including:
   one or more transducer segments comprising an array of transducer elements; and
   a probe controller in communication with the array of transducer elements to enable selection of a first subset of transducer elements of the array to transmit acoustic waveforms, and selection of a second subset of transducer elements of the array to receive returned acoustic waveforms,
   wherein the first subset of transducer elements are arranged to transmit spatially and temporally encoded acoustic waveforms toward a target volume in the biological subject and the second subset of transducer elements are arranged to receive the returned acoustic waveforms that return from at least part of the target volume, and
   wherein the acoustic probe is operable to transmit the acoustic waveforms on the first subset of transducer elements and the second subset of transducer elements in accordance with a predetermined transmit delay pattern that spatially and temporally encodes transmit waveforms such that each of the returned acoustic waveforms is distinguishable from another, such that the returned acoustic waveforms are decodable by isolating transmission of the acoustic waveforms transmitted by the first subset of transducer elements on reception by the second subset of transducer elements that correspond to a set of image points scattered from the target volume in the biological subject,
   wherein the predetermined transmit delay pattern comprises a set of random time delays,
   wherein the set of random time delays corresponds to a uniform distribution of random values within a range spanning from zero to a maximum tolerated standoff distance of the array of transducer elements.

9. The acoustic probe of claim 8, wherein the first subset of transducer elements is different from the second subset of transducer elements.

10. The acoustic probe of claim 8, wherein the first subset of transducer elements is the same as the second subset of transducer elements.

11. The acoustic probe of claim 10, wherein the second subset of transducer elements attenuates a transmit crosstalk signal to reduce image artifacts.

12. The acoustic probe of claim 8, wherein the acoustic waveforms have different amplitudes for each transmission.

13. The acoustic probe of claim 8, wherein acoustic waveforms have different phases for each transmission.

14. The acoustic probe of claim 8, wherein different frequency- coded or phase-coded waveforms are used for each transmission.

15. A method of signal transmission, comprising:
generating spatially and temporally encoded acoustic waveforms for interrogation of a target volume in a biological subject by:
transmitting, by a first transducer element on an array of transducer elements, after a time delay associated with the first transducer element, acoustic waveforms towards the target volume in the biological subject;
receiving, by a second transducer element on the array of transducer elements, after a round-trip time between the first transducer element and the second transducer element, returned acoustic waveforms that return from at least part of the target volume;
decoding the returned acoustic waveforms to isolate transmission of the acoustic waveforms transmitted by the first transducer element on reception by the second transducer element that correspond to a set of image points scattered from the target volume in the biological subject; and
processing the decoded returned encoded acoustic waveforms to beamform isolated echo samples for each image point of the set of image points of the target volume,
wherein the time delay is selected from a set of random time delays,
wherein the set of random time delays corresponds to a uniform distribution of random values within a range spanning from zero to a maximum tolerated standoff distance of the first and second transducer elements.

16. The method of claim 15, wherein the first transducer element is different from the second transducer element.

17. The method of claim 15, wherein the first transducer element is the same as the second transducer element.

18. The method of claim 17, wherein the second transducer element attenuates a transmit crosstalk signal to reduce image artifacts.

19. The method of claim 15, wherein the acoustic waveforms have different amplitudes for each transmission.

20. The method of claim 15, wherein acoustic waveforms have different phases for each transmission.

21. The method of claim 15, wherein different frequency- coded or phase-coded waveforms are used for each transmission.

22. A method for spatial and temporal encoding of acoustic waveforms in synthetic aperture acoustic imaging, comprising:
generating a set of spatially and temporally encoded acoustic waveforms for transmission toward a target volume that includes generating one or more of (i) a unique set of coded waveforms, (ii) a transmit delay pattern of time delays for acoustic waveforms to be transmitted at the target volume, or (iii) a transmit amplitude and phase pattern of the acoustic waveforms to be transmitted at the target volume;
coherently transmitting the spatially and temporally encoded acoustic waveforms, toward the target volume, using a spatially-sampled aperture formed on an array of transducer elements for one or more transducer segments of an acoustic probe device, wherein each transducer element used in the transmitting is assigned a first index number 1 to i, wherein i is a number equal to or less than a total number of transducer elements;
receiving returned encoded acoustic waveforms on the spatially-sampled aperture, wherein the transducer elements are assigned a second index number 1 to j, wherein j is a number equal to or less than the total number of transducer elements;
decoding the returned encoded acoustic waveforms to isolate the $i^{th}$ transmission on the $j^{th}$ reception that correspond to a set of image points scattered from the target volume; and
processing the decoded returned encoded acoustic waveforms to beamform isolated echo samples for each image point of the set of image points of the target volume,
wherein each time delay in the transmit delay pattern for the acoustic waveforms to be transmitted is selected from a set of random time delays,
wherein the set of random time delays corresponds to a uniform distribution of random values within a range spanning from zero to a maximum tolerated standoff distance between two or more transducer elements.

23. The method of claim 22, further comprising forming image of the target volume by processing data associated with the beamformed isolated echo samples.

24. The method of claim 22, wherein generating the transmit amplitude and phase pattern of the acoustic waveforms includes modulating an amplitude and modulating a phase for each acoustic waveform to be transmitted with respect to a transducer element index or a spatial position of the transducer element.

25. The method of claim 22, wherein the encoded acoustic waveforms have different amplitudes for each transmission.

26. The method of claim 22, wherein encoded acoustic waveforms have different phases for each transmission.

27. The method of claim 22, wherein the unique set of coded waveforms includes arbitrary waveforms that simultaneously satisfy properties of range compression and orthogonality.

* * * * *